(12) United States Patent
Milne et al.

(10) Patent No.: US 9,881,367 B1
(45) Date of Patent: Jan. 30, 2018

(54) IMAGE PROCESSING TECHNIQUES FOR PLUNGER DEPTH MEASUREMENT

(71) Applicant: AMGEN INC., Thousand Oaks, CA (US)

(72) Inventors: Graham F. Milne, Venture, CA (US); Thomas Clark Pearson, Newbury Park, CA (US); Erwin Freund, Camarillo, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

(21) Appl. No.: 15/672,494

(22) Filed: Aug. 9, 2017

(51) Int. Cl.
| | |
|---|---|
| *G06K 9/00* | (2006.01) |
| *G06T 7/00* | (2017.01) |
| *G06T 7/11* | (2017.01) |
| *G06T 7/13* | (2017.01) |
| *G06T 7/33* | (2017.01) |
| *G06K 9/62* | (2006.01) |
| *G06T 7/50* | (2017.01) |
| *A61M 5/315* | (2006.01) |

(52) U.S. Cl.
CPC .............. *G06T 7/001* (2013.01); *A61M 5/315* (2013.01); *G06K 9/6202* (2013.01); *G06T 7/11* (2017.01); *G06T 7/13* (2017.01); *G06T 7/337* (2017.01); *G06T 7/50* (2017.01); *A61M 2209/02* (2013.01); *G06T 2207/10028* (2013.01)

(58) Field of Classification Search
None
See application file for complete search history.

(56) References Cited

U.S. PATENT DOCUMENTS

| | | | | |
|---|---|---|---|---|
| 6,685,678 B2* | 2/2004 | Evans | ................. | G06F 19/3468 604/200 |
| 7,074,209 B2* | 7/2006 | Evans | ................. | G06F 19/3468 235/375 |
| 7,115,113 B2* | 10/2006 | Evans | ................. | G06F 19/3468 235/375 |
| 7,499,581 B2* | 3/2009 | Tribble | ................. | B65B 3/003 250/577 |
| 7,814,731 B2* | 10/2010 | Bender | ................. | B65B 57/10 53/276 |
| 8,037,659 B2* | 10/2011 | Osborne | ............... | A61J 1/2096 250/577 |
| 8,209,941 B2* | 7/2012 | Osborne | ............... | A61J 1/2096 53/237 |
| 8,763,651 B2* | 7/2014 | Stavsky | ................. | A61J 1/2096 141/18 |

(Continued)

*Primary Examiner* — Soo Park
(74) *Attorney, Agent, or Firm* — Marshall, Gerstein & Borun LLP

(57) ABSTRACT

An automated visual inspection (AVI) system is described to measure the depth of plungers positioned within vessels. The AVI system implements various types of image processing as well as other techniques to identify, for a vessel, a reference point and the uppermost edge of the plunger. Because different inconsistencies and/or artifacts may be introduced within the vessel image, different processing techniques may be executed on the region containing the reference point versus the plunger region. In doing so, the AVI system provides a robust means to accurately measure plunger depth that is highly resilient to the aforementioned artifacts and consistently measures plunger depth for a wide variety and types of vessels.

20 Claims, 11 Drawing Sheets

(56) References Cited

U.S. PATENT DOCUMENTS

| | | | |
|---|---|---|---|
| 9,746,093 B2* | 8/2017 | Peret | G06K 9/2027 |
| 9,746,094 B2* | 8/2017 | Peret | F16K 27/00 |
| 2012/0273087 A1* | 11/2012 | Stavsky | A61J 1/2096 |
| | | | 141/2 |
| 2016/0234464 A1* | 8/2016 | Loce | H04N 7/183 |
| 2016/0259913 A1* | 9/2016 | Yu | A61M 5/31 |

* cited by examiner

IMAGE PROCESSING TECHNIQUES FOR PLUNGER DEPTH MEASUREMENT

FIELD OF THE DISCLOSURE

The present application relates generally to image processing techniques used as part of an automated visual inspection (AVI) system to measure the depth of plungers positioned within vessels that are optionally placed in semi-translucent trays.

BACKGROUND

AVI systems are used in the clinical packaging environment for quality control purposes. In particular, AVI systems may be used to test syringes, such as those used in auto-injector pens, for example, for the proper plunger (i.e., rubber piston or stopper) depth. For auto-injector syringes, the position of the plunger within the syringe is of particular importance, as a plunger depth falling outside of a specified range of depth measurements may cause the auto-injector to malfunction or provide an incorrect dosage. For example, if the plunger is positioned too low in the syringe (i.e., towards the needle) the spring-activated piston used by the auto-injector pen may travel a longer distance before contact, thereby gathering excessive kinetic energy. This may produce a shockwave down the glass body of the syringe upon contact with the plunger, resulting in glass-breakage near the tapered needle-end. Moreover, plunger depth measurement is an important check in controlling the filling process and ensuring container closure integrity.

Traditional AVI systems measure plunger depth by identifying a top edge of the syringe flange and a top edge of the plunger, determining the difference between these two edges in terms of pixels, and then converting the pixel value to a linear real-world measurement based upon a conversion factor. However, due to the manufacturing process, glass syringe flanges typically have a somewhat uneven and unpredictable shape, and may include undulations that make it difficult for typical image processing algorithms to accurately identify the flange top edge. Furthermore, because the testing procedure is often conducted in an area that is not a cleanroom environment, dust or debris may settle on the syringe flange, causing traditional image processing techniques to incorrectly identify the top edge of the flange as an area associated with such artifacts. Further compounding this problem, defects in the trays holding the syringes may carry over into the image being analyzed, and typical image processing techniques may incorrectly identify such defects in the tray as the top edge of the flange.

Regarding the measurement of the top edge of the plunger, conventional image analyses such as edge detection function to identify the top and side edges of the plunger within a fixed region of interest (ROI). Using this information, conventional AVI systems typically identify the plunger centerline and use the intersection of the centerline with the top edge of the plunger as a reference by which to measure the plunger depth from the top edge of the flange. However, these techniques are constrained by the use of a fixed ROI, and therefore such conventional systems may only be used to test a single size and type of syringe. Furthermore, tray features used to secure each syringe within the tray may partially obscure the plunger and/or the operator may fail to align the syringes properly, causing edge detection techniques to fail. Further complicating this issue, blemishes on the syringe container wall and/or plunger dimples that exist along the top edge of the plunger may cause typical edge-detection algorithms to fail or to incorrectly identify the uppermost edge of the plunger. As a result, typical AVI systems used for syringe testing have several drawbacks.

SUMMARY OF THE DISCLOSURE

Embodiments described herein are directed to an AVI system that measures the depth of plungers positioned within a vessel (e.g., a syringe or cartridge). In doing so, the AVI system described herein may function to reduce the improper rejection of tested vessels while ensuring that a business adheres to regulatory and compliance testing guidelines within an acceptable level of business risk. The AVI system described herein may include a stage that accepts either a single vessel or a tray of vessels. In some embodiments, a linear motorized system may incrementally advance each vessel within the field of view of an imager to sequentially acquire and test each vessel using image processing in conjunction with other processing techniques. In other embodiments, several vessels may be imaged at one time with a wider field of view. Once an image of a particular vessel (or several vessels) is acquired via the imager, the AVI system described herein executes a series of image processing algorithms on different regions within the acquired image. In the event that the vessel being tested is a syringe, the image processing algorithms may result in the identification of a y-coordinate for the uppermost edge of the syringe flange and the syringe plunger. Once identified, the AVI system may measure the difference between these y-coordinate values in terms of pixels, and then convert this pixel value to a real-world measurement, which represents the plunger depth.

To overcome the aforementioned issues related to identifying the uppermost edge of the flange, the AVI system may identify a flange ROI within the image of the syringe and binarize the flange ROI using a technique referred to as blob analysis. The AVI system may perform additional image processing algorithms to reduce artifacts such as a closing algorithm that includes pixel dilation, hole-filling, and erosion, and use a horizontal row-scanning and linking technique to fill in voids of fragmented blob fragments. Upon completion of this image processing, the AVI system may identify an uppermost edge of the flange within the processed binarized image, thereby ensuring an accurate identification even in the presence of dust, debris, tray defects, flange inconsistencies, etc.

To overcome the aforementioned issues related to identifying the uppermost edge of the plunger, the AVI system may identify a plunger ROI within the image of the vessel and use a template-matching algorithm to mathematically match the plunger to a smaller template image. Once this template is identified, the AVI system may refine the original plunger ROI by aligning, or tethering, the matching template over the image of the plunger. This refined plunger ROI allows a more detailed analysis to be performed at the top of the plunger, which may not be completely flat and/or perpendicular to the inner glass wall, but include dimples or other artifacts such as tray protrusions. To address these artifacts, the AVI system may execute a series of one-dimensional (1D) edge detections that are evenly spaced across the top of the plunger using the refined ROI as a guide. This series of 1D edge detections produces an array of y-coordinate values, with a y-coordinate value being assigned to each evenly-spaced division. The array of y-coordinate values may be further constrained via a filtering process to remove outliers (i.e., y-coordinate values that deviate substantially from the flat portion of the top of the plunger). The uppermost edge of the plunger may then be accurately calculated and used as reference point for measuring plunger depth using this constrained set of y-coordinate values.

BRIEF DESCRIPTION OF THE DRAWINGS

The skilled artisan will understand that the figures, described herein, are included for purposes of illustration and are not limiting on the present disclosure. The drawings are not necessarily to scale, emphasis instead being placed upon illustrating the principles of the present disclosure. It is to be understood that, in some instances, various aspects of the described implementations may be shown exaggerated or enlarged to facilitate an understanding of the described implementations. In the drawings, like reference characters throughout the various drawings generally refer to functionally similar and/or structurally similar components.

Moreover, because the embodiments described herein are directed to image processing techniques, several images have been attached to this disclosure as part of an Appendix for clarity, in the event that these images would not otherwise be accepted as formal drawings. Some of these images represent an equivalent black and white line drawing from the Figures described below. For ease of explanation, this equivalence is noted where applicable in the accompanying Appendix.

DETAILED DESCRIPTION

The various concepts introduced above and discussed in greater detail below may be implemented in any of numerous ways, and the described concepts are not limited to any particular manner of implementation. Examples of implementations are provided for illustrative purposes.

Figure 1:
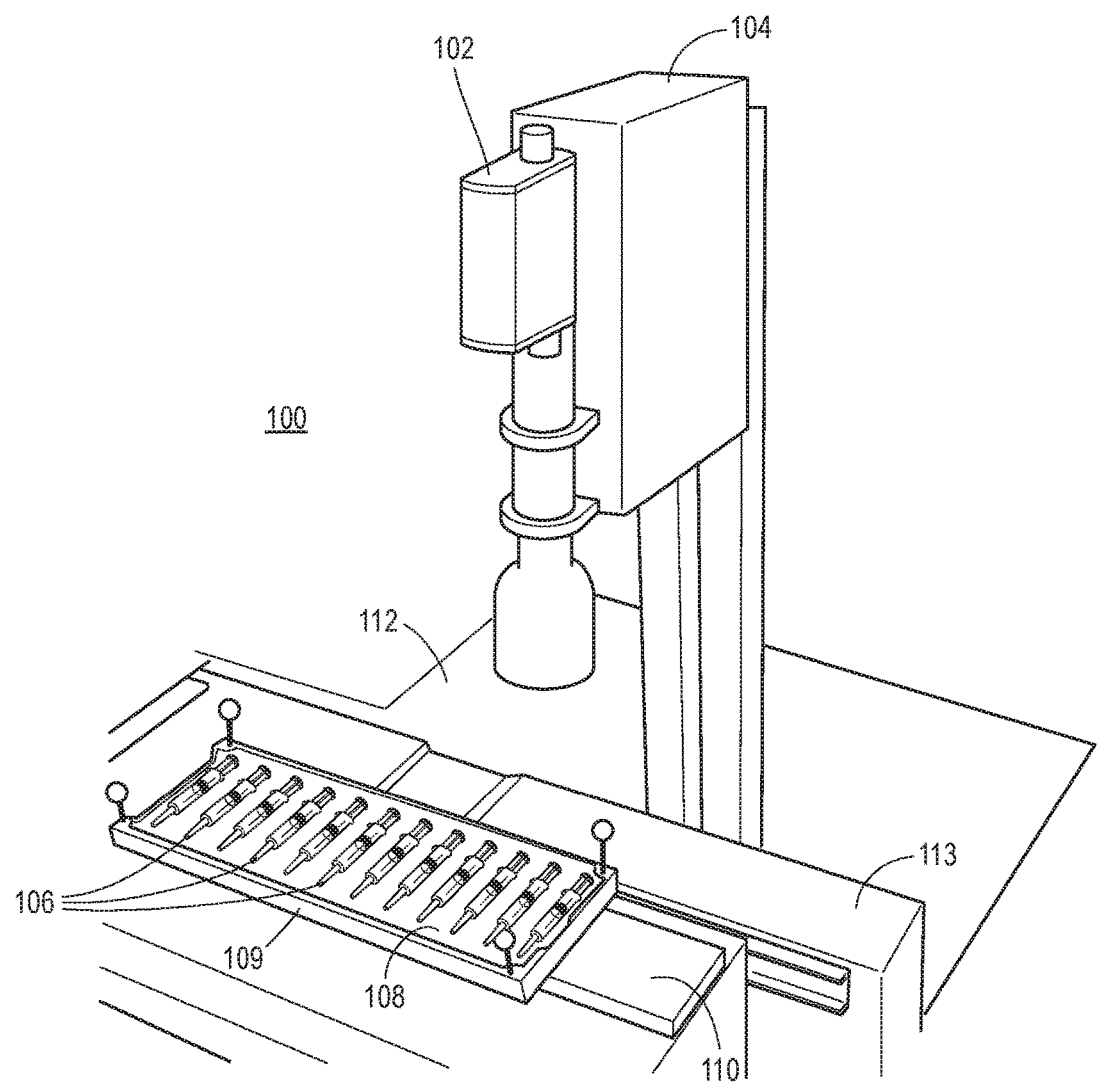
FIG. 1 illustrates an automated visual inspection (AVI) system 100, according to an embodiment of the present disclosure.

FIG. 1 illustrates an automated visual inspection (AVI) system 100, according to an embodiment of the present disclosure. The AVI system 100 includes a stage 112, to which various components of the AVI system 100 are mounted, including a controller 104 that may contain the various electronic communication, control, and/or processing components used in accordance with the embodiments as described herein, which are further discussed below with reference to FIG. 2.

The AVI system 100 may also include a tray holder 109. As shown in FIG. 1, the tray holder 109 is illustrated as being configured to receive a tray 108 including one or more vessels 106. As discussed herein, the operation of AVI system 100 is described in terms of measuring plunger depth within a syringe. However, the AVI system 100 may be implemented to measure plunger depth in any suitable type of vessel having a plunger, such as cartridges, for example. Thus, tray holder 109 may be implemented, in various embodiments, as a modular component to facilitate plunger depth measurements for a wide variety of vessel sizes and/or types. For example, the trays 108 may be implemented as fluted trays, such as those manufactured by Rondo-Pak, Inc. of Camden, N.J., and may be sized to hold a total of 17 syringes having a maximum volume of 2.25 mL each, a total of 20 syringes having a maximum volume of 1 mL each, etc. Thus, embodiments include the AVI system 100 utilizing a tray holder 109 of any suitable size and shape to accommodate different trays and vessels, and to firmly hold the tray of vessels in a fixed position during testing regardless of the size and number of vessels contained within the tray 108.

As further discussed below, embodiments include the AVI system 100 operating in an iterative manner, i.e., sequentially measuring the plunger depth of each vessel 106 contained in the tray 108 in accordance with the various image processing techniques discussed herein. To do so, the AVI system 100 may include a linear drive mechanism 113, which is coupled to the stage 112 and to the tray holder 109. The linear drive mechanism 113 may be implemented as any suitable type of motor-driven system that can be reliably and consistently align the vessels 106 beneath the imager 102. For example, the linear drive mechanism 113 may be implemented as a modularized component having an integrated motor, controller, amplifier, encoder, and communication bus, such as the Smartmotor SM23165D, manufactured by Moog Animatics of Mountain View, Calif. To provide another example, linear drive mechanism 113 may be implemented as any suitable type of conveyor belt (e.g., a translucent conveyor belt) configured to advance the tray 108 for plunger depth measurement. Of course, certain components may need to be adapted to changes for conveyor belt systems. For example, a vision-guided camera (not shown) may be implemented to scan each vessel in a stop-and-go matter, unless the camera moves briefly with the conveyor belt before moving back to its origin.

In embodiments, the imager 102 may include any suitable number and/or type of digital cameras and/or optical elements configured to acquire an image of each vessel 106 as it is advanced within a field of view of the imager 102 of suitable quality and resolution for image processing. The imager 102 may include any suitable combination of hardware and/or software to facilitate this functionality, such as image sensors, optical stabilizers, image buffers, frame buffers, frame grabbers, charge-coupled devices (CCDs), complementary metal oxide semiconductor (CMOS) devices, etc. Furthermore, the imager 102 may include one or more telecentric lenses to provide image magnification of the vessels 106 that is independent of the vessel's distance or position in the field of view. Moreover, the imager 102 may communicate with the controller 104 (as discussed below with reference to FIG. 2), and send acquired images to the controller 104 for image processing. Alternatively, the imager 102 may store the acquired images locally in any suitable type of memory, and this memory may be accessed by the controller 104 for image processing.

To provide another example, the imager 102 may be implemented as a "smart camera," with image processing logic built into the camera using any suitable techniques, such as field programmable gate array (FPGA) technologies, for example. To provide yet another example, the imager 102 may be implemented as part of a plenoptic 3D camera system. To provide a specific example of an implementation of the imager 102, the camera portion of the imager 102 may be implemented as an industrial area scan camera unit with a Gigabit Ethernet communication interface, such as the piA2400-17gm industrial monochrome camera manufactured by Basler, AG of Ahrensburg, Germany, which records images at a resolution of 5MP. To provide another specific example of an implementation of the imager 102, the imager 102 may utilize a telecentric lens manufactured by Edmund Optics of Barrington, N.J., having part. no. 62-933 and providing a 0.28× magnification. Using the example implementations of the Basler camera in conjunction with the Edmund Optics telecentric lens described above, the imager 102 may acquire images having a spatial resolution of approximately 12 microns per pixel.

To implement syringe imaging, the AVI system 100 may also include a light source 110 that is mounted beneath the imager 102, which illuminates the area behind the tray 108 as each vessel 106 is imaged. This light source may be implemented as any suitable number and/or type of lighting units configured to provide a sufficiently uniform and bright source of light for the imager 102. For example, the light source 110 may be implemented as a high-uniformity LED manufactured by CCS America, Inc., of Burlington, Mass., having part no. TH-83X75RD.

The controller 104 may include one or more components configured to communicate with and/or control the linear drive mechanism 113, the light source 110, and the imager 102. Thus, the controller 104 may command the linear drive mechanism 113 to selectively move the tray holder 109, and thus the vessels 106 contained in the tray 108, within a field of view beneath the imager 102, to activate the light source 110, and to acquire an image of each vessel 106 for image processing and plunger depth measurement. As each vessel 106 is tested in this manner, the AVI system 100 may also notify a user in the event that the plunger depth measurement is outside of an acceptable specified range of values with any suitable type of alert or warning system, which is not shown in FIG. 1 for purposes of brevity.

Although the AVI system 100 is shown in FIG. 1 as receiving the tray 108 and advancing the vessels 106 in a horizontal manner, embodiments include the AVI system 100 being configured to sequentially image vessels 106 in any suitable orientation and/or direction. For example, the linear drive mechanism 113, the tray holder 109, and the light source 110 may be mounted vertically with respect to the stage 112, whereas the imager 102 may be mounted horizontally, allowing for the vessels 106 to be advanced and imaged in the vertical direction.

Furthermore, AVI system 100 is described as performing plunger depth measurements of various vessels in terms of linearly incrementing the tray 108 and taking individual images of each vessel 106 in turn. However, the embodiments described herein are not limited to such embodiments. For example, imager 102 may implement optics to provide a wider field of view such that an image of any suitable number of vessels may be simultaneously captured within a single image, with the embodiments including applying the algorithms discussed herein to each of the individual vessels included in the same image. Moreover, in some embodiments, the tray 108 and tray holder 109 may be omitted or modified such that a single vessel 106 is imaged at one time.

Figure 2:
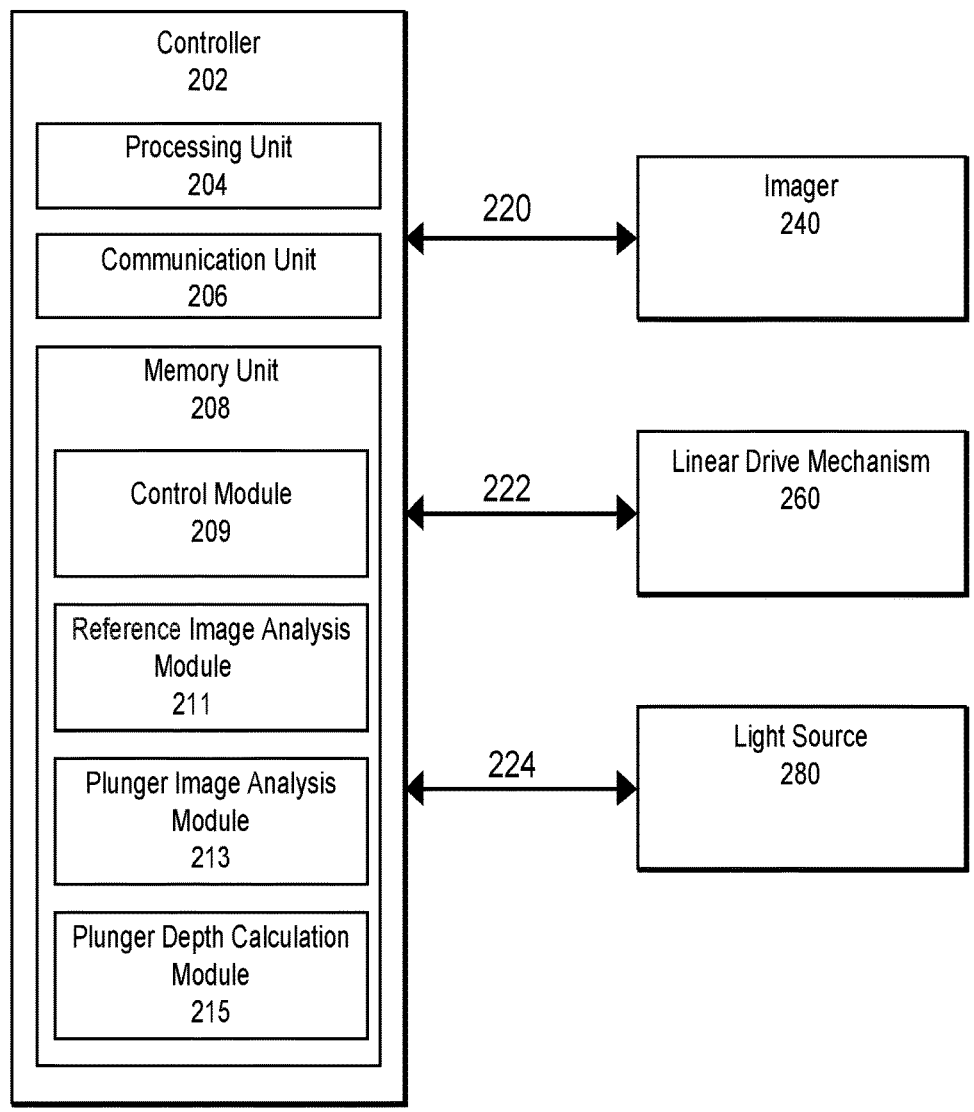
FIG. 2 is a block diagram example illustrating a control system 200 associated with AVI system 100, according to an embodiment of the present disclosure.

FIG. 2 is a block diagram example illustrating a control system 200 associated with AVI system 100, according to an embodiment of the present disclosure. As further discussed below, control system 200 may include a controller 202 that is configured to communicate with and control various components of AVI system 100, such as imager 240, linear drive mechanism 260, and/or light source 280, for example. In an embodiment, controller 202, imager 240, linear drive mechanism 260, and light source 280 may be an implementation of controller 104, imager 102, linear drive mechanism 113, and light source 110, respectively, as discussed herein with respect to FIG. 1.

Furthermore, in an embodiment, control system 200 is configured to facilitate fully autonomous or semi-autonomous operation of AVI system 100. To do so, control system 200 may support performing automatic image analysis of a number of syringes that are included on a tray to measure the plunger depth for each syringe. Again, this syringe plunger depth measurement may then be compared to compare to a range of acceptable values (for each syringe tested), which may be established based upon the size and/or type of syringes being tested.

Controller 202 may be implemented, for example, as any suitable combination of hardware and/or software coupled to or otherwise in communication with one or more of imager 240, linear drive mechanism 260, light source 280, and/or other components of the AVI system 100. For example, the controller 202 may be implemented as device mounted to or integrated as part of stage 112, as shown in FIG. 1, or controller 202 may be located remote from AVI system 100. In any event, controller 202 may be coupled to one or more of the imager 240, the linear drive mechanism 260, and/or the light source 280 via wired links, wireless links, or any suitable combination thereof. Therefore, links 220, 222, and/or 224 may represent such links to facilitate communications between these components. Although three separate links 220, 222, and 224 are shown in FIG. 2, it will be understood that controller 202 may communicate with one or more of the imager 240, the linear drive mechanism 260, and/or the light source 280 via any suitable number of links, including a single shared link.

To facilitate communication with and/or control of these components, controller 202 may include a processing unit 204, a communication unit 206, and a memory unit 208. Processing unit 204 may be implemented as any suitable type and/or number of processors, such as a host processor of controller 202, for example. To provide additional examples, processing unit 204 may be implemented as an application specific integrated circuit (ASIC), an embedded processor, a central processing unit associated with controller 202, etc. Processing unit 204 may be coupled with and/or otherwise configured to communicate, control, operate in conjunction with, and/or affect operation of one or more of communication unit 206 and/or memory unit 208 via one or more wired and/or wireless interconnections, such as any suitable number of data and/or address buses, for example. These interconnections are not shown in FIG. 2 for purposes of brevity.

For example, processing unit 204 may be configured to retrieve, process, and/or analyze data stored in memory unit 208, to store data to memory unit 208, to replace data stored in memory unit 208, and/or to control various functions associated with the imager 240, the linear drive mechanism 260, and/or the light source 280. For example, the processing unit 204, alone or in conjunction with other components implemented by the controller 202 (some of which may not be shown in FIG. 2 for purposes of brevity), may cause linear drive mechanism 260 to advance a tray of syringes to be aligned with the imager 240, to activate the light source 280, to acquire syringe images, and to store the syringe images in any suitable portion of memory unit 208 (or another suitable storage device). Moreover, the processing unit 204, alone or in conjunction with other components implemented by the controller 202, may facilitate controller 202 analyzing the stored syringe images in accordance with the image processing techniques discussed herein, calculating a plunger depth based upon this image processing, determining whether the measured plunger depth is within a range of acceptable values, and notifying a user of these results in any suitable manner. Additional details associated with such functions are further discussed below.

Communication unit 206 may be configured to support any suitable number and/or type of communication protocols to facilitate communications between controller 202 and one or more of imager 240, linear drive mechanism 260, and/or light source 280. Communication unit 206 may be configured to facilitate the exchange of any suitable type of information between controller 202 and one or more of these components (e.g., via links 220, 222, and/or 224), and may be implemented as any suitable combination of hardware and/or software to facilitate such functionality. For example, communication unit 206 may be implemented with any number of wired and/or wireless transceivers, buffers, modems, ports, input/output interfaces, connectors, antennas, etc.

In accordance with various embodiments, memory unit 208 may be a computer-readable non-transitory storage device that may include any suitable combination of volatile (e.g., a random access memory (RAM), or non-volatile memory (e.g., battery-backed RAM, FLASH, etc.). Memory unit 208 may be configured to store instructions executable on processing unit 204. These instructions may include machine readable instructions that, when executed by processing unit 204, cause processing unit 204 to perform various acts as described herein. Although the various functions of controller 202 are described herein in terms of execution of instructions stored in memory unit 208 via processing unit 204, it will be understood that equivalent functions may be realized exclusively via hardware components (e.g., circuit components) or hardware components (e.g., those implemented via communication unit 206) working in conjunction with processing unit 204 executing instructions stored in memory unit 208. Memory unit 208 may also be configured to store any other suitable data used in conjunction with AVI system 100, such as images captured by the imager 240.

The various modules stored in memory unit 208 may represent one or more applications (e.g., software, hardware, or combinations thereof) that are associated with different functions and/or carry out specific tasks associated with the operation of the AVI system 100, and thus are modularized in FIG. 2 for ease of explanation. These modules may represent, for example, one or more algorithms, logic and code, executable instructions, programs, general, specialized, or programmable hardware components, etc.

For example, control module 209 may be a region of memory unit 208 configured to store instructions, that when executed by processing unit 204, cause processing unit 204 to transmit one or more commands to and/or to receive information from one or more components of the AVI system 100. In an embodiment, processing unit 204 may execute instructions stored in control module 209 to read the current position of the linear drive mechanism 260 and transmit one or more commands (e.g., via link 222) to the linear drive mechanism 260 to advance the tray 108 and position the next syringe beneath the imager 240. Furthermore, instructions stored in the control module 209 may cause the controller 202 to transmit one or more commands to the light source 280 (e.g., via link 224) to control the state of the light source 280, which may include turning the light source on and off, adjusting the wavelength and/or intensity of light, etc.

Figure 3:
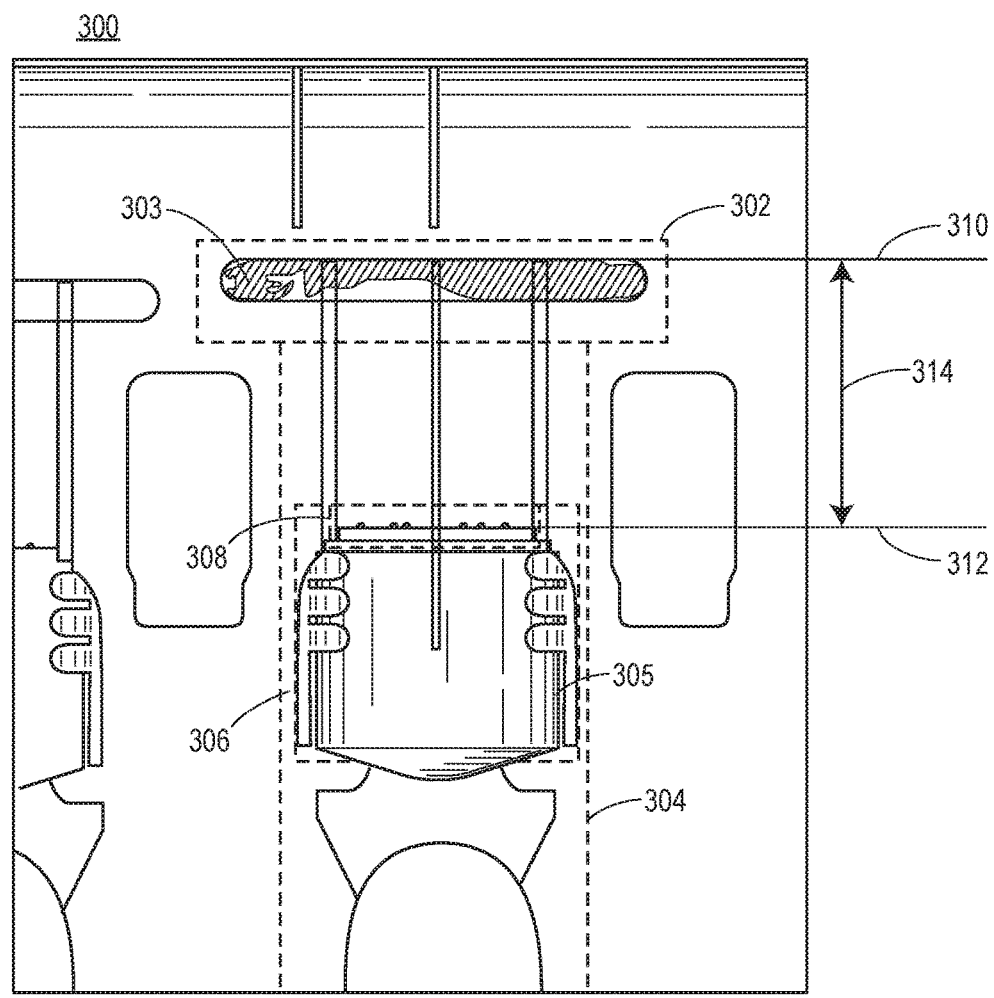
FIG. 3 is an example of an acquired image of a syringe 300, according to an embodiment of the present disclosure.

Still further, instructions stored in the control module 209 may cause the controller 202 to transmit one or more commands to the imager 240 to control the state of the imager 240, which may include acquiring and storing vessel images. An example of one such image is shown in FIG. 3 as syringe image 300, which is further referenced herein for ease of explanation. In particular, syringe image 300 may be referenced to describe the image processing techniques used to measure the plunger depth 314, which is represented in FIG. 3 as a difference between the uppermost edge of the flange 310 and the uppermost edge of the plunger 312.

Reference image analysis module 211 is a region of memory unit 208 configured to store instructions, that when executed by processing unit 204, cause processing unit 204 to perform various acts in accordance with applicable embodiments as described herein. In an embodiment, reference image analysis module 211 includes instructions that, when executed by processing unit 204, cause processing unit 204 to analyze a vessel image acquired by the imager 240 to identify a reference or anchor point suitable to measure plunger depth. For example, if syringes are being imaged, reference image analysis module 211 may include instructions that, when executed by processing unit 204, cause processing unit 204 to identify the uppermost edge of a syringe flange within the image. To provide another example, if cartridges are being imaged, reference image analysis module 211 may include instructions that, when executed by processing unit 204, cause processing unit 204 to identify a terminal or distal edge of the glass cartridge body within the image. In either case, this may be defined in any suitable manner. For example, an anchor point may be established as the "highest" point (i.e., y-coordinate of the highest pixel) of a flange's upper surface or the highest point associated with the upper edge of the cartridge relative to the body axis of the syringe. In the example of a syringe being imaged, this is indicated by the uppermost edge of the flange 310, as shown in FIG. 3.

Defining the uppermost edge of the flange in this manner allows it to be identified in spite of any flange undulations. To do so, flange image analysis module 211 may include instructions that enable processing unit 204 to identify a flange region of interest (ROI) 302 within the overall syringe image 300 that encompasses the flange 303. In embodiments, the flange ROI 302, as well as the other ROIs within the syringe image 300, may be identified to improve the efficiency of the image processing operations. In other words, the use of ROIs allow image processing to be performed on a smaller portion of the vessel image rather than the entire image, which is unnecessary and would require a much greater use of processing resources and time to do so.

In various embodiments, any suitable reference point ROI, such as the flange ROI 302 in this example, may be identified in any suitable manner. For example, processing unit 204 may localize the flange ROI 302 by identifying the largest dark feature within a predefined larger region of the syringe image 300. The flange image 300 also includes other ROIs, such as an initial, or coarse, plunger ROI 304, as well as refined plunger ROIs 306 and 308. These plunger ROIs are discussed further below with reference to the image analysis techniques used to identify the uppermost edge of the plunger 312.

Once the flange ROI 302 is identified, embodiments include the processing unit 204 executing instructions stored in flange image analysis module 211 to perform various image processing operations to determine the uppermost edge of the flange 310. In an embodiment, an initial image processing step includes applying a threshold value to the reference point ROI (e.g., the flange ROI) to create a "binarized" image. Continuing this example, once the flange ROI has been binarized, adjacent pixels of similar value can be organized into continuous objects, or blobs. Characteristics such as area, centroid position, and bounding edges may then be defined from the two-dimensional objects contained in the binarized image, which may be used to identify the uppermost edge of the flange.

In embodiments, this binarized image may be generated, for example, in accordance with blob analysis techniques, which compare the color value of each pixel to a threshold pixel color value, and set each pixel color value within the flange ROI to either a one (white) or zero (black) based upon this comparison. For example, for an 8-bit greyscale image, each pixel within the flange ROI may represents a color value between 0 (black) and 255 (white). A threshold color value may be selected between this scale of color values such that pixel color values below this threshold color value are set to a binary value of 0 (black), whereas pixel color values above this threshold color value are set to a binary value of 1 (white). In various embodiments, any suitable threshold color value may be chosen to suitably differentiate the flange within the flange ROI from the image background. For example, a threshold color value of 130/255 may be chosen such that pixel color values between 0-129 are set to black, whereas pixel color values between 130-255 are set to white.

Figure 4A:
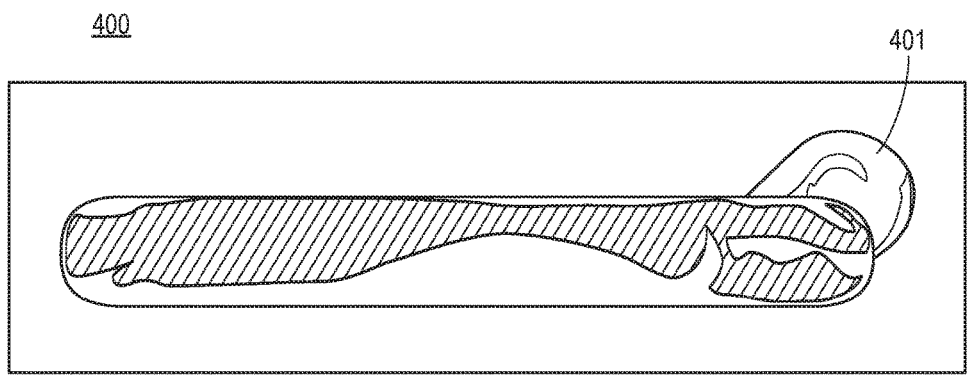
FIG. 4A is an example of a flange region of interest (ROI) 400 having a tray defect in the background, according to an embodiment of the present disclosure.
Figure 4B:
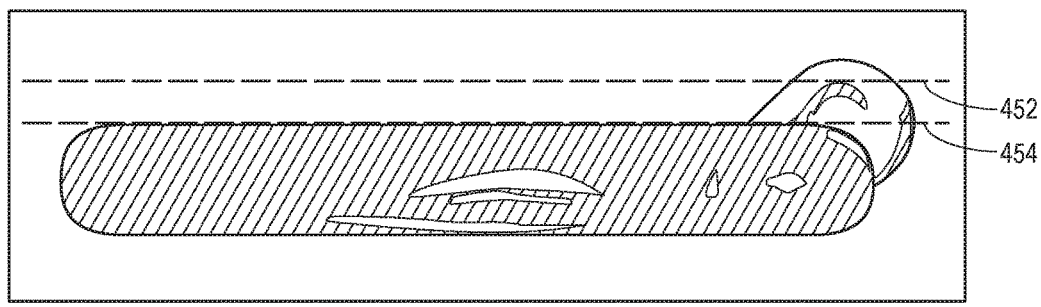
FIG. 4B is an example of a binarized flange ROI 450, which indicates a false uppermost edge of the flange due to the tray defect.

An example of the application of blob analysis to convert a flange ROI to a binarized image is shown in FIGS. 4A-4B. In particular, FIG. 4A shows a flange ROI 400 in greater detail, and FIG. 4B shows a binarized flange ROI 450 after the application of the blob analysis discussed above to the flange ROI 400. Because the flange ROI 400 includes a tray defect 401 in the background, this particular defect is also present in the binarized flange ROI 450. As a result, a conventional image processing analysis of the binarized flange ROI 450 would incorrectly identify the uppermost edge of the flange as line 452 instead of line 454.

In various embodiments, one or more image processing steps may be performed prior to converting the ROI to a binarized image, such as those shown in FIGS. 4A-4B, for example. For instance, some larger vessels (e.g., those with a maximum volume of 2.25 mL) may tend to become aligned with certain tray features. To provide an illustrative example, larger syringes may become oriented within a tray such that the flanges are positioned above a darker area of the tray within the image than that of smaller syringes. One reason for this alignment is the differences in vessel sizes as well as differences in tray designs to accommodate different types of syringes.

In any event, when a flange (or other reference point associated with another type of vessel) rests over a darker area of the tray within the image, a loss of contrast may introduce difficulties when attempting to identify the top edge of the flange. To remedy this, embodiments include first extracting the flange ROI, but applying a convolution of the flange ROI with one or more kernels if any suitable size and/or type. To provide an illustrative example, a 3×3 Sobel variant kernel, in accordance with a Labview coding application, may be implemented to perform this image processing operation. This produces an "edge" image that essentially highlights the top edges of the dark features in the original image. Once this convolution is performed, embodiments further include subtracting the convoluted (i.e., edge) image from the original image to darken the top edge of the flange and sharpening the contrast of the flange against the tray background. As a result, the subsequent distinction of the flange from the tray in the background can be performed more easily and in a more robust manner. An example of the images generated in accordance with this image processing step are shown in the last page of the Appendix. Once this image processing is performed, embodiments include binarizing the resulting image to produce the binarized ROI, as discussed herein.

Figure 5:
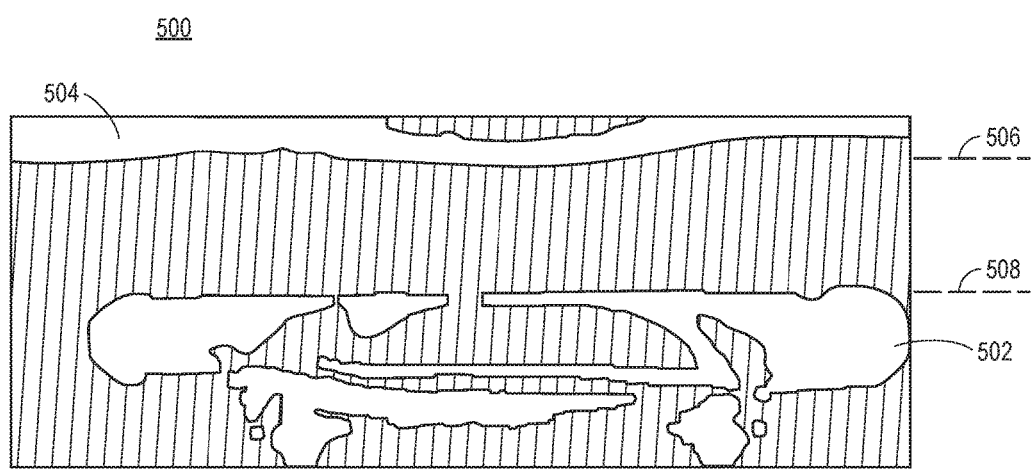
FIG. 5 is an example of a binarized flange ROI 500, which indicates a falsely identified uppermost edge of the flange due to blob fragmentation.

Other artifacts that are present in the flange ROI may also be introduced into the binarized flange ROI, and may likewise cause conventional image processing techniques to incorrectly identify the actual uppermost edge of the flange. For example, depending on the specific form of the glass and the rotational orientation of the vessel in the tray when imaged, the binarized flange ROI may vary substantially from one syringe to another. For example, as shown in FIG. 5, a fragmented binarized flange ROI 500 illustrates the result of blob fragmentation. In particular, the upper portion of the binarized flange ROI 500 includes several smaller blobs 502 that constitute the flange as well as a blob 504 that is caused by the tray in the background being imaged and binarized. To identify the uppermost edge of the flange, image processing techniques may assume that the largest continuous blob within the binarized flange ROI is associated with the flange. However, if the blob is fragmented and/or other artifacts are present in the binarized image, this may not necessarily be the case, as shown in FIG. 5. As a result, a conventional image processing analysis of the binarized flange ROI 500 would incorrectly identify the uppermost edge of the flange as line 506 instead of line 508, as blob 504 is the largest continuous blob within the binarized flange ROI 500.

Therefore, embodiments include processing unit 204 executing instructions stored in flange image analysis module 211 to perform one or more additional image processing operations to reliably identify the uppermost edge of the flange regardless of dust, debris, tray defects, fragmentation of the flange object, etc. In various embodiments, different metrics associated with the imaging system may be varied to counter many of these artifacts, which may be adjusted in combination with various image processing algorithms, as discussed below and elsewhere herein.

For example, backlight intensity, among other imaging parameters, may be adjusted to reduce background artifacts. Referring back to FIG. 1, this may include adjusting the light intensity associated with the light source 110 such that some of these artifacts are "bleached out," or reduced in size, which in turn increases the efficacy of the other image processing algorithms as discussed herein. Moreover, increasing the backlight intensity poses a small risk to the fidelity of the measurement, as extremities of the flange object (or other suitable portion of the imaged vessel, as the case may be) can also be bleached out. This may lead to an overall reduction in the size of the relevant object (e.g., the flange), as well as a reduction in the apparent measured position of the top edge. Therefore, embodiments include balancing the light intensity in any suitable manner, such as based upon the tray and/or vessel type being tested and/or via other imaging metrics, taking into consideration the biological product impact when relevant. To provide an illustrative example, an imager backlight intensity of 200-220 lx·hr. may suitably reduce artifacts in accordance with the embodiments as described herein. Furthermore, embodiments include one or more metrics associated with the imager (e.g., imager 102) being adjusted such as the aperture on the telecentric lens, the gain on the camera, and/or digital image processing techniques, in addition to or instead of increasing the illuminating intensity, to reduce artifacts.

Regardless of the imaging setup used to acquire images, once an image is acquired and binarized, embodiments include one or more image processing algorithms being additionally or alternatively performed on the initial binarized flange ROI to "close" the blobs, to remove artifacts, and help ensure that the largest continuous blob within the binarized flange ROI is, in fact, associated with the flange. In an embodiment, a "closing" algorithm may be executed by processing unit 204. To do so, embodiments include first applying a pixel dilation algorithm to the initial binarized flange ROI, such that the border of each blob is expanded in every direction by a set number of pixels to generate a dilated binarized flange image. This dilation may be performed over any suitable number of iterations (e.g., 6, 8, 10, etc.), with each iteration expanding the borders of each blob by one or more pixels. For instance, the dilation algorithm may be applied 8 times, with each iteration expanding the borders of the blobs contained in the binarized flange ROI by a single pixel, resulting in the blob borders being expanded by 8 pixels in each direction. Upon expanding the borders of each blob by one or more pixels, the closing algorithm may also include processing unit 204 executing a "fill-hole" algorithm to fill in cavities within each (now expanded) blob.

After the dilation and hole filling have been completed, the closing algorithm may further include processing unit 204 applying an erosion algorithm to the dilated and hole-filled binarized flange image to iteratively remove pixels from its edges by a set number of pixels for each successive iteration, thereby creating the binarized flange ROI. In an embodiment, the number of erosion iterations may be equal to the number of aforementioned dilation iterations, with each iteration reducing the borders of each blob by one or more pixels. Continuing the previous example, the erosion algorithm may be applied 8 times, with each iteration reducing the borders of the dilated and hole-filled binarized flange image by a single pixel, resulting in the blob borders being reduced by 8 pixels in each direction.

In some embodiments, processing unit 204 may apply a void-filling or "linking" algorithm to the blob fragments after the closing algorithm has been executed as described above. In other embodiments, the linking algorithm may be executed regardless of whether the closing algorithm has been performed. In any event, this linking algorithm may allow processing unit 204 to combine the blobs associated with the flange together with one another without combining them with blobs associated with the tray in the background. This may include, for example, horizontally scanning and linking individual rows within the blobs contained in the binarized flange image, which is now described in further detail with reference to the binarized flange image 600, as shown in FIG. 6A.

In an embodiment, the linking algorithm may include processing unit 204 scanning each individual horizontal row within the binarized flange image 600 in either direction (i.e., right-to-left or left-to-right). One of these scanned rows is shown in FIG. 6A as row 602, although embodiments include processing unit 204 repeating this process for each horizontal row contained in the binarized flange image 600. In an embodiment, the horizontal row may be associated with a single pixel dimension, thus allowing the processing unit 204 to perform a one-dimensional (1D) scan of each horizontal row on a pixel-by-pixel basis. As the row 602 is scanned (e.g., from left-to-right in the example shown in FIG. 6A), the processing unit 204 may identify the pixel value associated with each pixel in the binarized flange image 600 as having a value of 1 (i.e., white or another monochrome color) or a value of 0 (i.e., the black background).

Figure 6A:
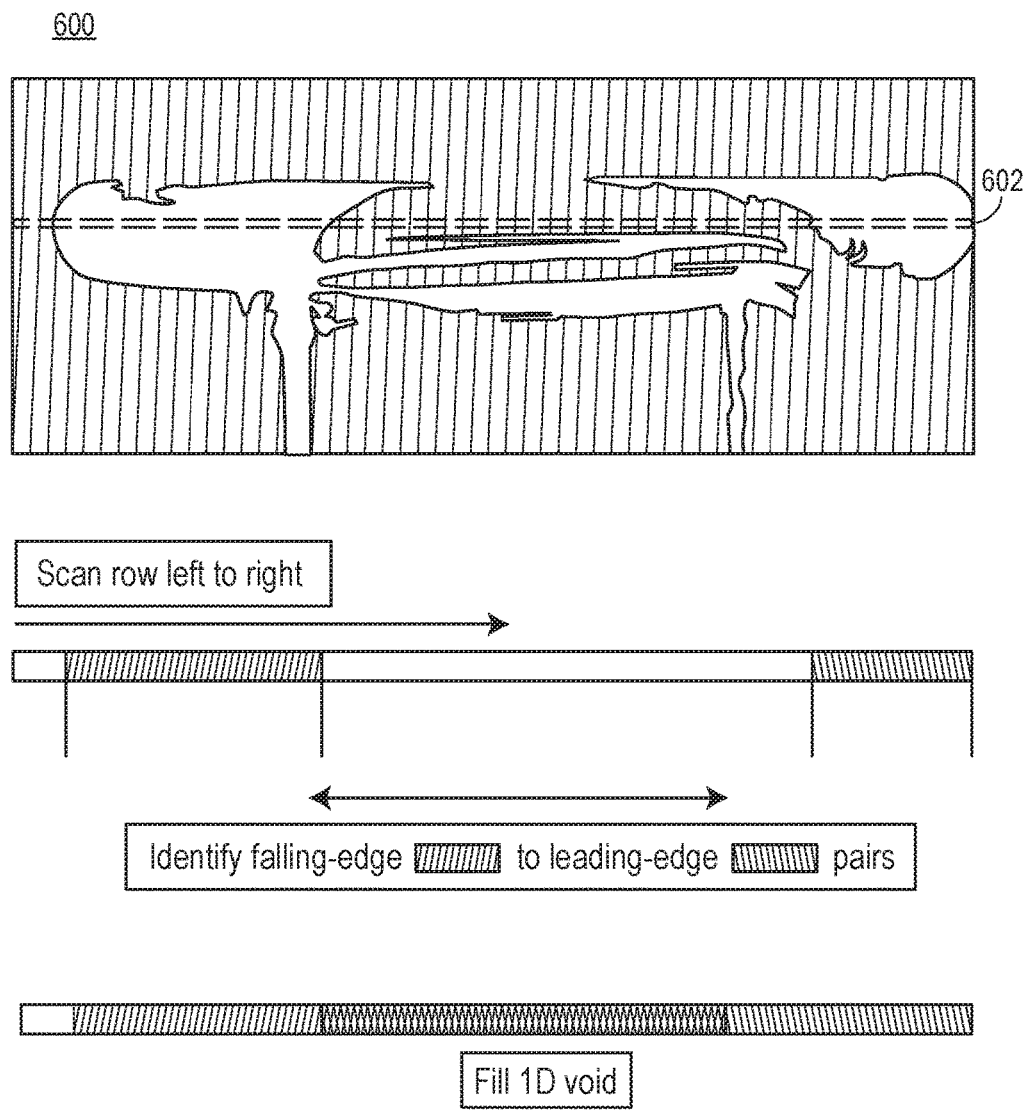
FIG. 6A is an example of a linking technique for a binarized flange ROI 600, according to an embodiment of the present disclosure.
Figure 6B:
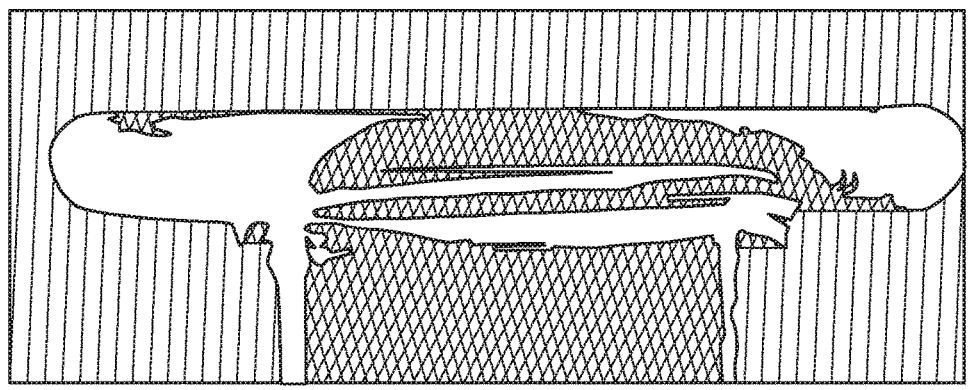
FIG. 6B is an example of a resulting void-filled binarized flange ROI 650 after applying the linking technique shown in FIG. 6A, according to an embodiment of the present disclosure.

In doing so, the processing unit 204 may further identify the location and occurrence of pixel binary value transitions from a binary value of 1 to a binary value of 0, which are referred to herein as "falling edges," as shown in FIG. 6A. Moreover, the processing unit 204 may identify the location and occurrence of pixel binary value transitions from a binary value of 0 back to a binary value of 1, which are referred to herein as "rising edges." Thus, as each horizontal row is scanned, falling and rising edge pixel pairs may be identified, and the 1D pixel space between these falling and rising edge pixel pairs may be "filled" or "linked" together. This linking process may include, for example, processing unit 204 setting, or otherwise adjusting, the pixel value of each pixel between adjoining falling and rising edge pixel pairs from a binary value of 0 to a binary value of 1, as shown in FIG. 6A for row 602. Upon each row within the binarized flange image 600 being scanned and filled in this manner, embodiments include the processing unit 204 generating a unified binarized flange image 650 that includes the pixels within each individually scanned horizontal row being adjusted in this manner, as shown in FIG. 6B. Thus, the process of executing the closing algorithm in conjunction with the linking algorithm may function to "close" each of the blobs contained in the binarized flange ROI to combine flange image fragments. Moreover, the "erosion" step described above with respect to the closing algorithm may further remove artifacts, such as dust and debris and other tray artifacts in the background. This ensures that the largest continuous blob is, in fact, associated with the flange, and thus the uppermost edge of the flange is accurately identified. In particular, once the unified binarized flange image is generated, embodiments include processing unit 204 storing the unified binarized flange image in memory unit 208 (or another suitable storage device), and identifying the uppermost edge of the syringe flange as shown in FIG. 3 (310) as the y-coordinate of the highest pixel within the unified binarized flange image associated with the largest continuous blob.

Plunger image analysis module 213 is a region of memory unit 208 configured to store instructions, that when executed by processing unit 204, cause processing unit 204 to perform various acts in accordance with applicable embodiments as described herein. In an embodiment, plunger image analysis module 213 includes instructions that, when executed by processing unit 204, cause processing unit 204 to analyze a syringe image acquired by the imager 240 to identify an uppermost edge of the plunger within the image. For the plunger, this may be defined in any suitable manner that utilizes a reference point from which plunger depth within a particular type of vessel may be measured. For example, the uppermost edge of the plunger may be defined as the center of the top edge of the plunger (excluding dimples and other small defects). Continuing this example, the uppermost edge of the plunger may be identified as a point in which the top edge of the plunger intersects with the body centerline of the syringe. This point may thus be identified as another y-coordinate at this location, which is then associated with the plunger's uppermost surface, as indicated by the uppermost edge of the plunger 312, as shown in FIG. 3.

Again, to measure the plunger depth from an acquired syringe image, the uppermost edge of the flange and the uppermost edge of the plunger are each detected. The embodiments used to implement detection of the uppermost edge of the flange were discussed above, and utilize specific image processing techniques to address issues related to image analysis of the flange region. Moreover, and as further discussed below, embodiments include executing one or more image processing techniques and/or other analyses to accurately identify the uppermost edge of the plunger, which presents its own set of issues that are addressed using different image processing techniques.

To do so, plunger image analysis module 213 may include instructions that enable processing unit 204 to "localize" the plunger within the image, which need not be binarized given the dark coloration of the plunger in contrast to the translucent flange. However, embodiments include the plunger being localized within the image in accordance with any suitable type of techniques, which may include via binarization (e.g., to the extent that the plunger is a larger, opaque object within a transparent or semi-transparent vessel), or the template-matching process as further described herein. In any event, the initial plunger ROI may be considered a "coarse" ROI, which corresponds to an area within the image that the plunger could reasonably be expected to be found. As discussed above with reference to FIG. 1, in some embodiments, each syringe may be sequentially advanced into the imager's field of view via the linear drive mechanism 113. In doing so, each syringe is centered within the imager's field of view to facilitate identification of the initial plunger ROI. In embodiments in which vessels are not incrementally imaged, any suitable techniques may be implemented to localize the plunger within each respective vessel image as needed. An example of an initial plunger ROI is shown in FIG. 3 within a syringe as initial plunger ROI 304, which includes the syringe body beneath the flange ROI 302 and encompasses the plunger 305.

Conventional image processing techniques perform plunger localization by analyzing the initial plunger ROI 304 for the largest dark feature, and then using the center-of-mass of this corresponding object to a calculate 3 smaller ROIs. Conventionally, two of these ROIs are established by determining the left and right edges of the corresponding object (i.e., the assumed plunger). A standard image processing technique known as edge detection is typically implemented to measure the position of these edges in each respective ROI. Then, a third ROI for the plunger top edge is defined using the plunger's apparent position within the image, which is then used to identify the top edge of the plunger. Once the plunger is localized in this manner, conventional image analyses using edge detection identify the top and side edges of the plunger within the ROI, identify the plunger centerline, and use the intersection of the centerline with the top edge of the plunger to measure the plunger depth from the top edge of the flange.

Figure 7:
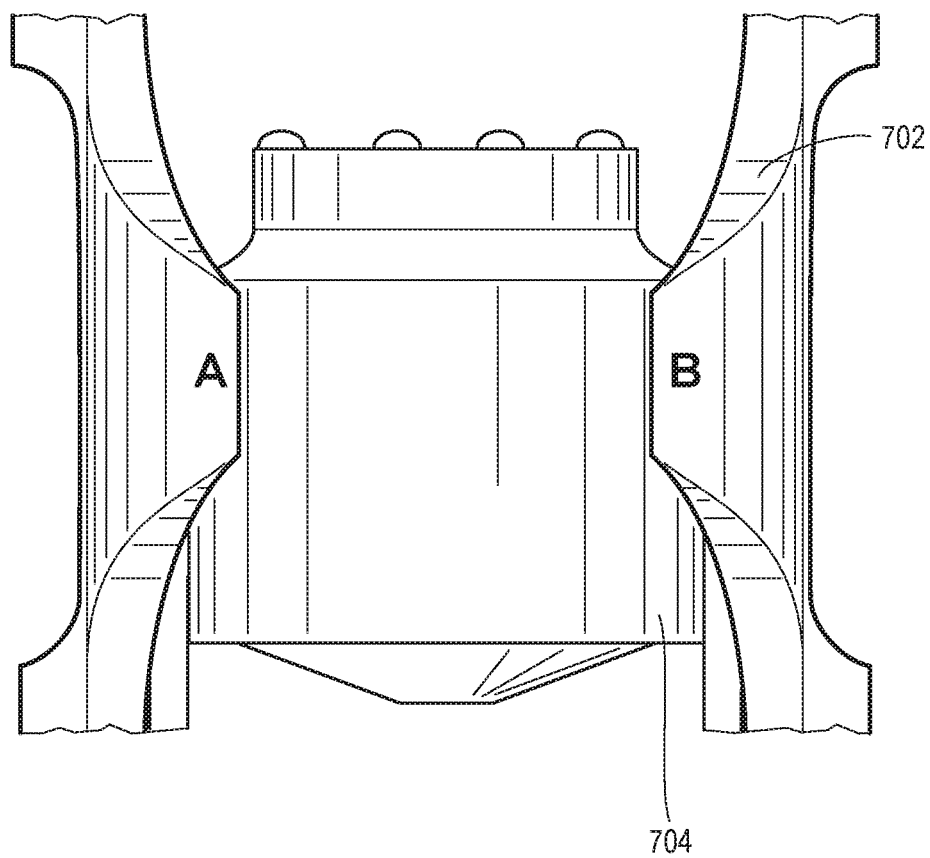
FIG. 7 is an example of a plunger ROI 700, which indicates tray protrusions that partially obscure the plunger, according to an embodiment of the present disclosure.

However, the aforementioned conventional image processing techniques do not work well over a range of vessel types and volumes, some of which may incorporate differing plunger designs. In particular, syringes with higher fill volumes (e.g., those filled in accordance with 2.25 mL volume vessels, which may have some fill volume that is a fraction thereof) have plungers that sit higher up (i.e., closer to the flange) than syringes with lower fill volumes. In such scenarios, these plungers may be positioned, when imaged, behind protruding features associated with the tray (e.g., tray 108), which serve to grip the syringe and hold it in place. If the plunger is located behind these features, it may be partially obscured, causing the traditional edge detection techniques described above to fail to adequately locate the plunger edges. This may result in inaccurate plunger top edge detection, or even prevent the plunger top edge from being detected. A plunger ROI 700 is shown in FIG. 7, and shows tray protrusions A and B that are part of the tray 702, which partially obscure the image of the plunger 704.

Therefore, to remedy this issue, embodiments include plunger image analysis module 213 including instructions that, when executed by processing unit 204, facilitate the execution of one or more template-matching algorithms to map refined ROIs (e.g., the refined ROIs 306 and 308, as shown in FIG. 3) within the initial (i.e., coarse) plunger ROI based upon the characteristics of a matching plunger image template. For example, memory unit 208 (or another suitable storage device accessible by the controller 202) may store several plunger image templates, which may be idealized theoretical templates or based upon real-world image samples, in various embodiments.

To provide an illustrative example, for a single type of syringe, several (e.g., 10, 50, 100, etc.) syringes may be imaged as part of a "training" process that is separate from the plunger depth image analysis techniques discussed herein. This training process may include processing the acquired images for a specific type of syringe design to mathematically average characteristics from these acquired images together to form an "ideal" plunger template. For example, for each syringe/plunger type (each syringe having a unique plunger), some number N (e.g., 100) of different plungers may be imaged, each localized within their respective initial plunger ROIs, and then cropped. Controller 202 may then execute an algorithm on each of the cropped plunger templates to identify various characteristics (e.g., geometric features and dimensions) in a manner such that subsequent plunger images can later be matched to their respective ideal plunger templates (which may also have tray protrusions present when imaged based upon real-world examples). The characteristics from each of these N number of cropped plunger templates may then be averaged to create an ideal plunger template that is specific to the particular type of plunger. This ideal plunger template is then stored in any suitable portion of controller 202 (e.g., memory unit 208) or external storage that may be accessible by controller 202. These ideal plunger templates may be stored with their respective identifying characteristic (e.g., as metadata stored with each ideal plunger template image).

Once the ideal plunger templates are created, embodiments include processing unit 204 executing instructions stored in plunger image analysis module 213 to identify a particular ideal plunger template image and any identifying characteristic data (e.g., the metadata described above), and matching the initial plunger ROI to an ideal plunger template using the characteristic data. That is, controller 202 may match a particular ideal plunger template to the current plunger image within the initial plunger ROI. This matching process may be implemented in any suitable manner, in various embodiments, such as using the metadata stored in the ideal plunger template image, as discussed above.

To provide an illustrative example, plunger matching may be executed via a greyscale value pyramid template matching algorithm. In any event, once the matching plunger template is identified, embodiments further include processing unit 204 identifying a further localized image of the plunger within the image of the syringe using the identified characteristics (e.g., dimensions and other detected features) of the matching template to the actual image of the plunger being analyzed. This localized region may be considered a refined ROI, such as refined ROI 306, for example, as shown in FIG. 3.

Additionally, once the plunger has been localized within the refined ROI using template matching, embodiments include processing unit 204 executing instructions stored in plunger image analysis module 213 to align a further refined plunger ROI to the top of the plunger within the refined ROI. For example, because key geometric features are known for the matching template image, embodiments may include overlaying the matching plunger template over the image of the plunger.

Figure 9A:
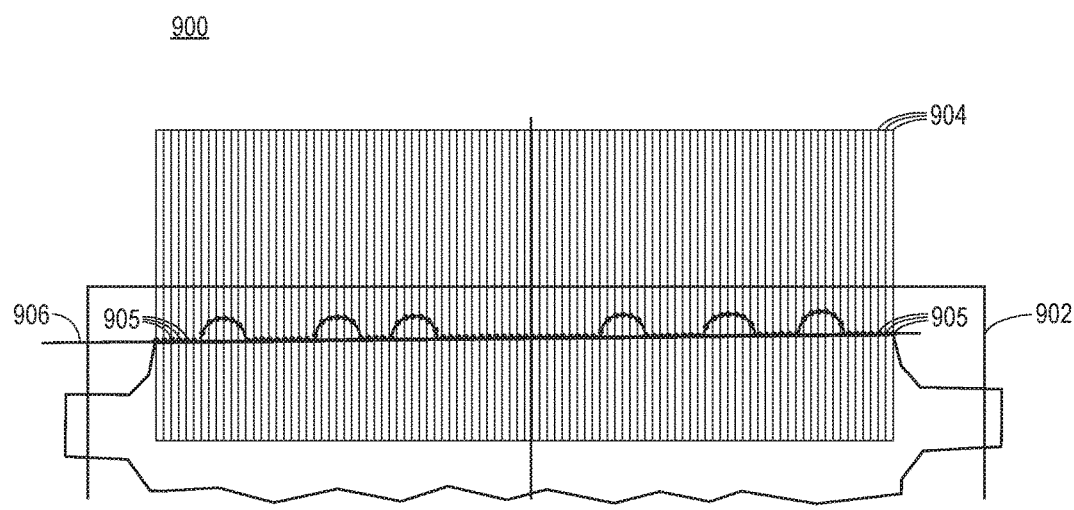
FIGS. 9A-9B are example images 900 and 950, respectively, of a refined plunger ROI that is aligned with the top of the plunger to facilitate one-dimensional (1D) edge detection, according to an embodiment of the present disclosure.

To provide an illustrative example, embodiments include processing unit 204 executing instructions stored in plunger image analysis module 213 to execute a plunger matching algorithm, as discussed above, to identify a matching ideal plunger template. The characteristic data that is associated with this matching ideal plunger template may further include a set of coordinates defining a bounding box. In an embodiment, this set of coordinates may be utilized as the basis for the refined ROI and to anchor and align the further refined ROI within the already refined ROI. In doing so, key features such as shapes and edges of the plunger template may be mapped to those same features in the plunger image, allowing the further refined ROI to be identified and aligned with the top of the plunger that encompasses the top edge of the plunger in even finer detail. This further refined ROI may include, for example, the refined ROI 308 as shown in FIG. 3, or the refined ROI 902 as shown in FIG. 9A, the latter of which is further discussed below.

Figure 8A:
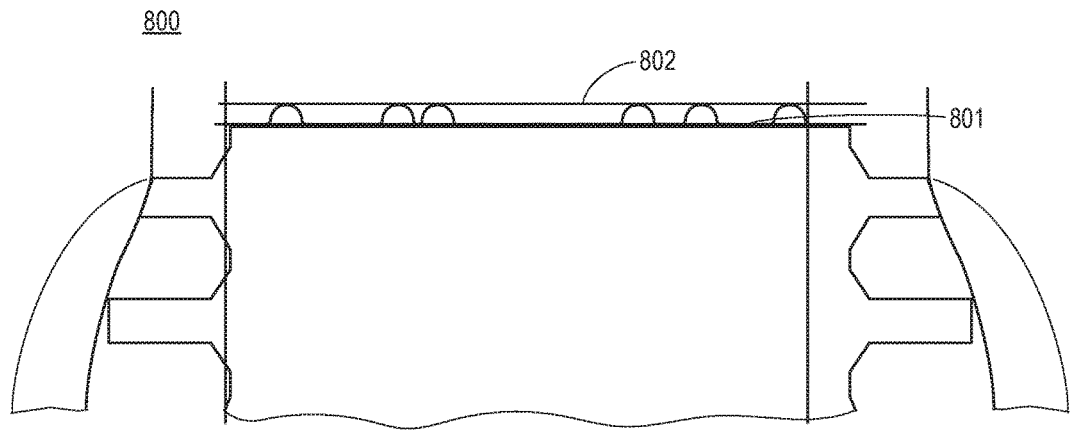
FIGS. 8A-8B are example images 800 and 850, respectively, of a top portion of a plunger indicating an incorrectly identified uppermost edge of the plunger.
Figure 8B:
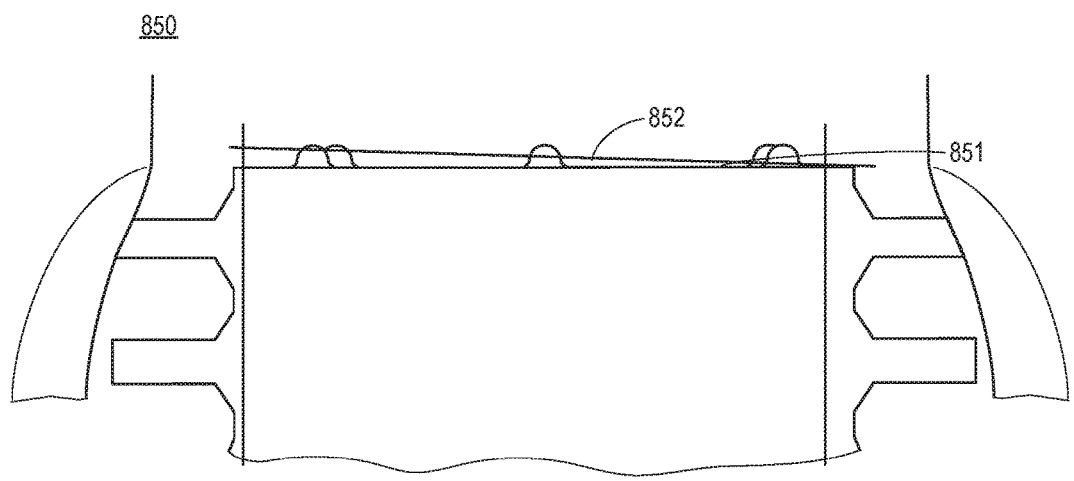

Again, some plungers may have small dimples or other imperfections, which present additional issues when using image processing techniques to identify the plunger's top edge. Two examples of the difficulties of conventional image processing systems to properly identify the top edges of a plunger are shown in the images 800 and 850 of FIGS. 8A and 8B, respectively. For example, performing conventional edge detection upon the image 800, as shown in FIG. 8A, results in the calculation of an incorrectly-identified top edge 802, which is offset from the actual uppermost edge of the plunger 801 by the height of the dimples. Moreover, performing conventional edge detection upon the image 850, as shown in FIG. 8B, results in the calculation of the incorrectly-identified top edge 852, which is misaligned with the uppermost edge of the plunger 851.

Therefore, to address these issues, embodiments include processing unit 204 executing instructions stored in plunger image analysis module 213 to perform post-processing operations on data identified within the refined and aligned ROI (i.e., using template matching), as discussed above. An example of such post-processing operations is described with reference to FIGS. 9A-9B. For example, FIG. 9A shows an example of a refined ROI 902 for an image 900 of a plunger, as discussed above. Embodiments include processing unit 204 performing a series of one-dimensional (1D) edge detections evenly spaced across the top of the plunger ROI 902, and filtering the y-coordinates obtained in this manner to identify the uppermost edge of the plunger 906.

Figure 9B:

To provide an illustrative example, the refined ROI 902 may be divided into a number of evenly-spaced columns 904, each of which may be occupied by one or more pixels. In an embodiment, each column 904 may have a single pixel-width to facilitate a 1D edge detection algorithm that is iteratively executed in the vertical direction (i.e., top-to-bottom or perpendicular to the top surface of the plunger as shown in FIGS. 9A-9B), within each column, across the top surface of the plunger. As a result, processing unit 204 may calculate, for each single-pixel width column 904, a single y-coordinate value corresponding to the edge detection algorithm's highest ranking score for a falling edge (bright-to-dark) along that particular edge. These y-coordinate values are represented in FIG. 9A as dots 905.

However, performing the 1D edge detection within each of the columns 904 produces y-coordinate values (905) that track the outline of the plunger, which may include any artifacts, such as dimples, for example. Therefore, embodiments include processing unit 204 executing instructions stored in plunger image analysis module 213 to filter these results to produce a y-coordinate value that accurately and reliably corresponds to the uppermost edge of the plunger 906. This filtering process may be performed in accordance with any suitable filtering techniques, such as averaging, a histogram analysis, weighted averaging, statistical analysis, mean height analysis, etc.

In an embodiment, processing unit 204 may generate a 1D array from the individual y-coordinate values (905), which may represent y-coordinate values organized by their corresponding x-coordinate (i.e., horizontal position) within the refined ROI 902 from left to right. In addition, the y-coordinate values contained in the 1D array may then be binned in accordance with a histogram according to these y-coordinate values. In various embodiments, any suitable number of histogram bins may be selected based upon the expected variation amongst the y-coordinate values (e.g., 5, 10, 15, 20, 25, etc.). Then, bins having less than a threshold number of y-coordinate value entries, or elements, may be discarded. As a result of using histogram binning in this manner, outlying y-coordinate values (e.g., those that excessively deviate from a mean height due to dimples or other artifacts) may be removed from the 1D array. An example of the filtered y-coordinate values as a result of this process is represented in FIG. 9B by the box 952, which demonstrates a constrained set of y-coordinate values that are refined by mean height in accordance with the histogram binning technique described above.

This process of filtering, or constraining, the y-coordinate values may be repeated any suitable number of times to achieve a final cull of y-coordinate values for calculating the uppermost edge of the plunger 906. Once the 1D array has been filtered in this manner, the statistical majority of points in the 1D array now represent plunger heights within a small range of a maximum value, which can now be associated with the top edge of the plunger and not the dimples or other artifacts. Regardless of how many iterations of filtering are performed on the 1D array to generate a set of constrained values, embodiments include processing unit 204 executing instructions stored in plunger image analysis module 213 to apply a best-fit-line algorithm to the constrained set of y-coordinate values. The output of this best-fit algorithm may then generate a line that is used as the uppermost edge of the plunger 906.

Plunger depth calculation module 215 is a region of memory unit 208 configured to store instructions, that when executed by processing unit 204, cause processing unit 204 to perform various acts in accordance with applicable embodiments as described herein. In an embodiment, plunger depth calculation module 215 includes instructions that, when executed by processing unit 204, cause processing unit 204 to calculate a plunger depth from an acquired image of a syringe by determining the difference in y-coordinate values from the uppermost edge of the flange and the uppermost edge of the plunger, as discussed above. Once this difference is known, processing unit 204 may further execute instructions stored in plunger depth calculation module 215 to convert the y-coordinate value, which may be measured in terms of pixels, to a real-world measurement based upon a calibrated conversion factor. This conversion factor may be based upon characteristics of the acquired image and associated components, such as the spatial resolution of the acquired image, for instance. Once known, this measured depth value may be compared to a range of acceptable values, and this process may be repeated for any suitable number of syringes, such as each syringe in an entire tray, for example. Again, the controller 202 may notify a user to a syringe having a plunger depth outside of a specified range, which may be implemented via processing unit 204 executing instructions stored in plunger depth calculation module 215.

Figure 10:
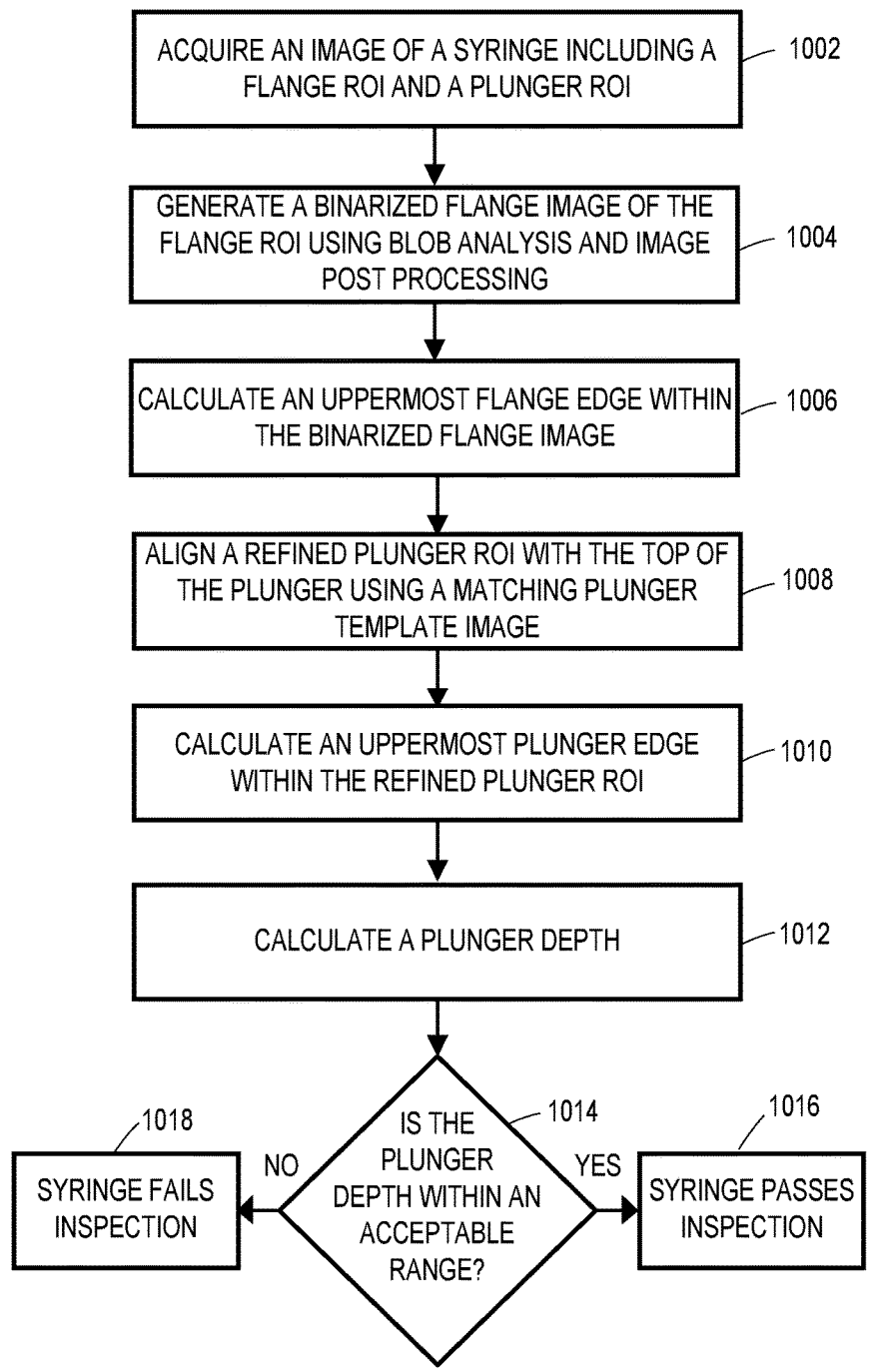
FIG. 10 illustrates an example of a method flow 1000 for testing the proper syringe plunger depth, according to an embodiment of the present disclosure.

FIG. 10 illustrates an example of a method flow 1000 for testing the proper syringe plunger depth, according to an embodiment of the present disclosure. In various embodiments, one or more regions of method 1000 (or the entire method 1000) may be implemented by any suitable device. For example, one or more regions of method 1000 may be performed by controller 202, imager 240, linear drive mechanism 260, and/or light source 280, as shown in FIG. 2, working independently or in conjunction with one another. Method 1000 represents the various steps performed during the testing of a single syringe, which may be repeated any suitable number of times for multiple syringes, and may include iteratively testing each syringe within a tray (e.g., tray 108, as shown in FIG. 1).

Method 1000 may begin when one or more processors acquire an image of a vessel, such as a syringe, for example (block 1002). This image may be, for example, one of several sequential images acquired during testing of several syringes on a tray, as discussed above with reference to the AVI system 100 shown in FIG. 1 (block 1002). This acquired image may also include, for example, an image of a syringe including a flange ROI and a plunger ROI, as shown and discussed with reference to FIG. 3.

Method 1000 may include one or more processors generating a binarized flange image of the flange ROI using blob analysis and image post processing (block 1004). This may include, for example, the various image processing techniques to close fragmented flange blobs and to reduce artifacts and blob fragments, as discussed above with reference to FIGS. 4A-B and 5 (block 1004). This may also include, for example, performing a horizontal linking algorithm on the fragmented flange blobs to combine them with one another, as discussed above with reference to FIGS. 6A-B (block 1004).

Method 1000 may include one or more processors calculating an uppermost flange edge within the binarized flange image (block 1006). This may include, for example, identifying the y-coordinate associated with highest pixel within the binarized flange image after post processing operations have been applied (block 1004) to the flange ROI (block 1006).

Method 1000 may include one or more processors aligning a refined plunger ROI with the top of the plunger using template matching (block 1008). This may include, for example, identifying a matching plunger template and using the characteristics included in the matching plunger to template to align one or more refined ROIs with the top of the plunger (block 1008). For example, this may include generating and aligning refined ROIs 306 and 308 with the top of the plunger within the initial ROI 308, as discussed above with reference to FIG. 3 (block 1008).

Method 1000 may include one or more processors calculating an uppermost plunger edge within the refined plunger ROI (block 1010). This may include, for instance, dividing the top surface of the plunger image into one pixel-wide columns, performing 1D edge detection within each column, and filtering the y-coordinate values obtained in this manner, as discussed herein with reference to FIGS. 9A-9B (block 1010).

Method 1000 may include one or more processors calculating a plunger depth (block 1012). This may include for example, calculating the plunger depth using the difference in y-coordinate values from the uppermost edge of the flange (block 1006) and the uppermost edge of the plunger (block 1010), as discussed herein (block 1012). Method 100 may also include converting this y-coordinate value to a real-world measurement based upon a calibrated conversion factor (block 1012).

Method 1000 may include one or more processors determining whether the plunger depth is within an acceptable range (block 1014). This may include, for instance, comparing the calculated plunger depth (block 1012) to a specified range of acceptable plunger depths, which may be based upon the particular type and/or size of the vessel being tested (block 1014).

If the measured plunger depth is within the acceptable specified depth, then method 1000 may continue to indicate that the syringe being tested passes inspection (block 1016). This may include, for example, advancing the next vessel for testing, causing a notification to be issued (e.g., illuminating a green light or displaying a suitable indicator, sounding a "passing" tone, etc.), or otherwise continuing testing until either every syringe in the tray has been tested or one of the vessels fails inspection.

In the event that the plunger depth is outside of an acceptable range, method 1000 may continue to indicate that the vessel being tested has failed inspection (block 1018). Additionally, a vessel may fail inspection in the event that a tray is missing one or more vessels, or a particular incremental test indicates that an expected vessel is not present (block 1018). This may additionally or alternatively include, for example, pausing the testing, causing a notification to be issued (e.g., illuminating a red light or displaying a suitable indicator, sounding a "fail" tone, etc.), or otherwise notifying a user of the failed status (block 1018). In some embodiments, vessel testing may continue regardless of whether some vessels fail inspection, with a report indicating at the end of the tray being tested those vessels that failed and their corresponding plunger depth measurements (block 1018). In other embodiments, method 1000 may stop each time a vessel fails inspection (block 1018).

Some of the Figures described herein illustrate example block diagrams having one or more functional components.

It will be understood that such block diagrams are for illustrative purposes and the devices described and shown may have additional, fewer, or alternate components than those illustrated. Additionally, in various embodiments, the components (as well as the functionality provided by the respective components) may be associated with or otherwise integrated as part of any suitable components. For example, the controller 302 may be integrated with the illumination system 340 or the imager 380.

Many examples discussed herein refer to the measurement of plunger depth with reference to a syringe. Again, it will be understood that the embodiments discussed herein may be applied to any suitable type of plunger depth measurement within any suitable type of vessel for which AVI systems may be implemented. For example, plunger depth may be measured within cartridges that may be placed onto trays in a similar manner as syringes.

Additionally, the embodiments described herein are directed to measuring plunger depth within various types of vessels (e.g., syringes and cartridges). For ease of explanation, this technique has been described by primarily focusing upon the identification of the uppermost edge of a reference or anchor point on the vessel (e.g., the uppermost edge of the flange) and the plunger. However, the embodiments described herein are not limited to these examples, and any suitable reference point may be identified to facilitate plunger depth measurements in accordance with the embodiments. For example, a bottom reference or anchor point within the vessel may be identified as opposed to the top reference or anchor point (e.g., the lowermost edge of the vessel), with the lowermost edge of the plunger likewise being identified to enable the calculation of the plunger depth.

Embodiments of the disclosure relate to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as ASICs, programmable logic devices ("PLDs"), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

As used herein, the singular terms "a," "an," and "the" may include plural referents unless the context clearly dictates otherwise.

As used herein, relative terms, such as "above," "below," "up," "left," "right," "down," "top," "bottom," "vertical," "horizontal," "side," "higher," "lower," "upper," "over," "under," "inner," "interior," "outer," "exterior," "front," "back," "upwardly," "lower," "downwardly," "vertical," "vertically," "lateral," "laterally" and the like refer to an orientation of a set of components with respect to one another; this orientation is in accordance with the drawings, but is not required during manufacturing or use.

As used herein, the terms "connect," "connected," and "connection" refer to an operational coupling or linking. Connected components can be directly or indirectly coupled to one another, for example, through another set of components.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, technique, or process to the objective, spirit and scope of the present disclosure. All such modifications are intended to be within the scope of the claims appended hereto. While the techniques disclosed herein have been described with reference to particular operations performed in a particular order, it will be understood that these operations may be combined, sub-divided, or re-ordered to form an equivalent technique without departing from the teachings of the present disclosure. Accordingly, unless specifically indicated herein, the order and grouping of the operations are not limitations of the present disclosure.

APPENDIX
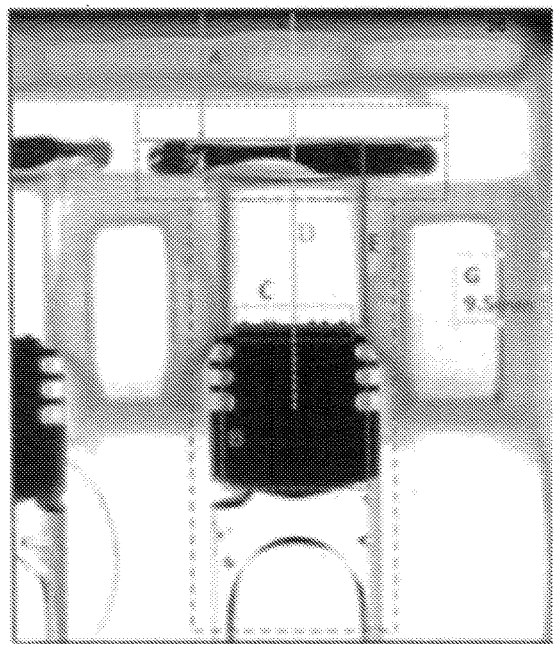
*The image above is equivalent to the black and white line drawing of an example acquired image of a syringe 300, as shown in FIG. 3. Several ROIs are also identified in the image as dashed lines, and a plunger depth measurement (9.5 mm) is also included.*

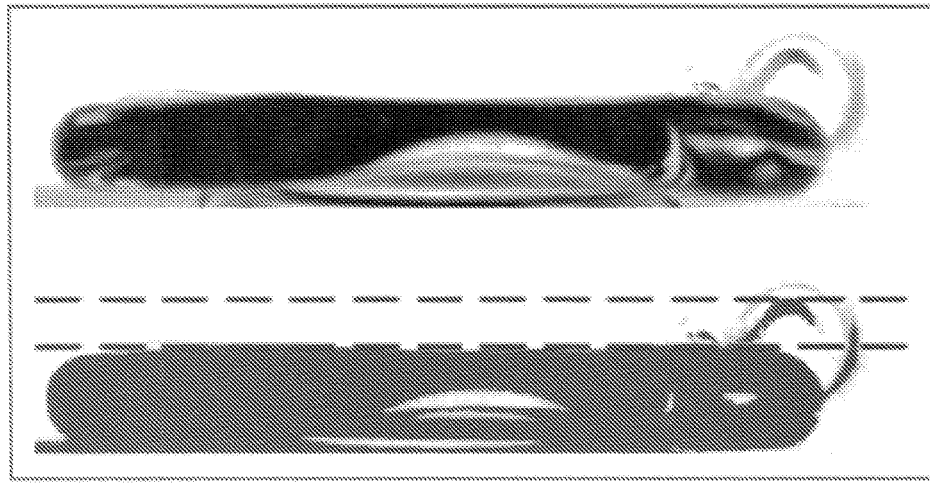

*The top image above is equivalent to the black and white line drawing of an example flange ROI 400 having a tray defect in the background, as shown in FIG. 4A.*

*The bottom image above is equivalent to the black and white line drawing of an example binarized flange ROI 450 indicating a false uppermost edge of the flange due to the tray defect, as shown in FIG. 4B.*

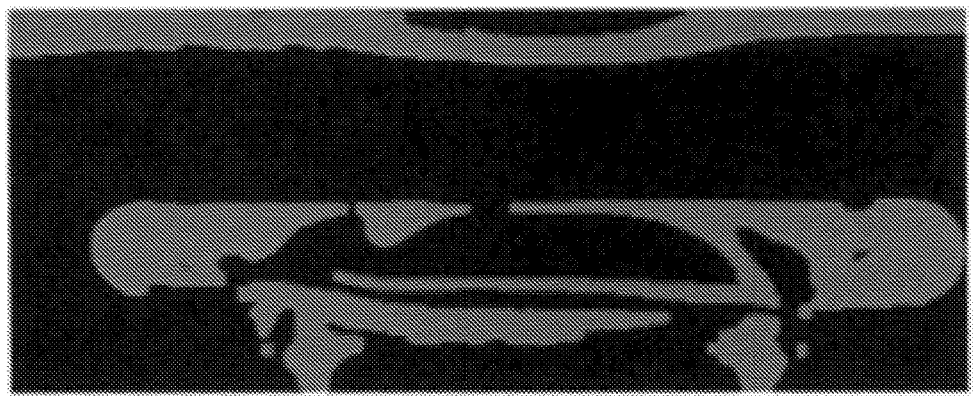

*The image above is equivalent to the black and white line drawing of an example binarized flange ROI 500, which indicates a falsely identified uppermost edge of the flange due to blob fragmentation, as shown in FIG. 5.*

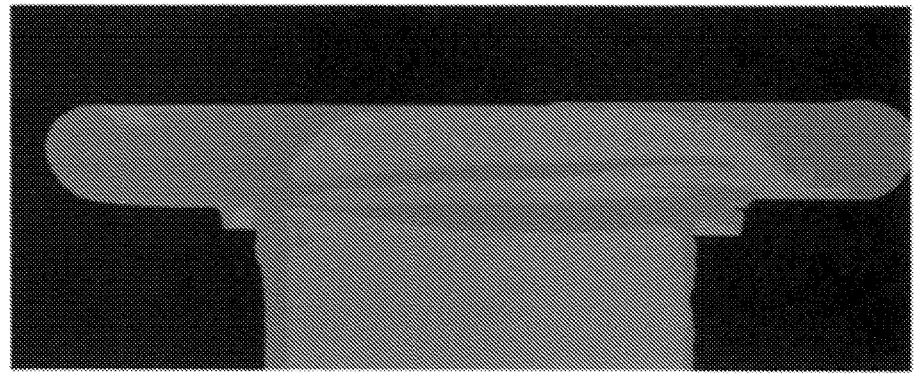
*The image above is equivalent to the black and white line drawing of an example void-filled binarized flange ROI 650, as shown in FIG. 6B.*
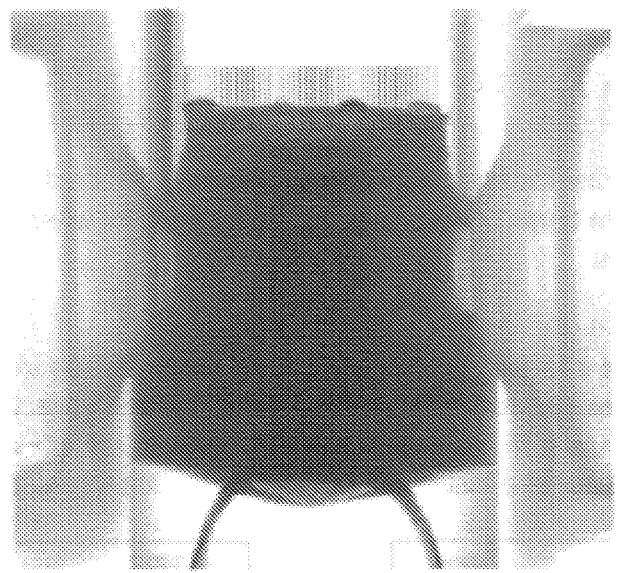
*The image above is equivalent to the black and white line drawing of an example plunger ROI 700, which indicates tray protrusions that partially obscure the plunger, as shown in FIG. 7.*

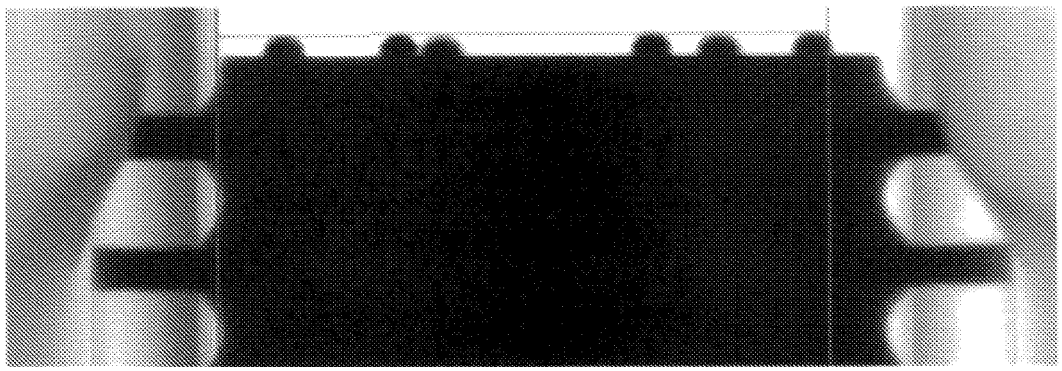

The image above is equivalent to the black and white line drawing of an example image 800 of a top portion of a plunger indicating an incorrectly identified uppermost edge of the plunger, as shown in FIG. 8A.

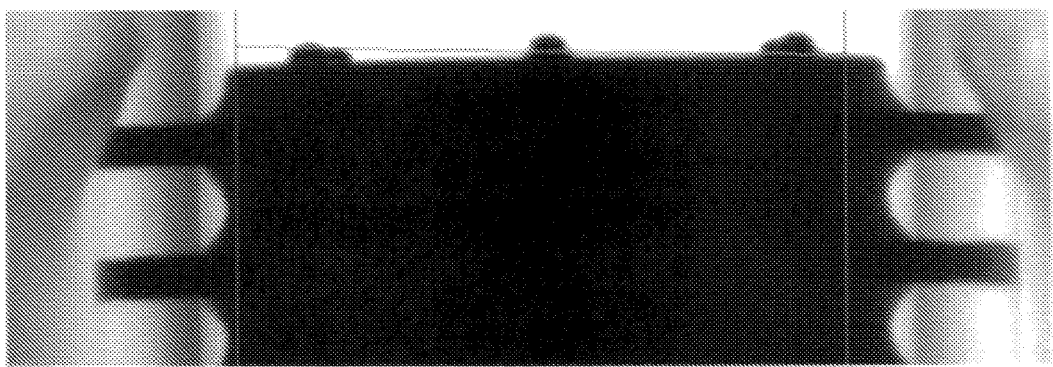

The image above is equivalent to the black and white line drawing of an example image 850 of a top portion of a plunger indicating an incorrectly identified uppermost edge of the plunger, as shown in FIG. 8B.

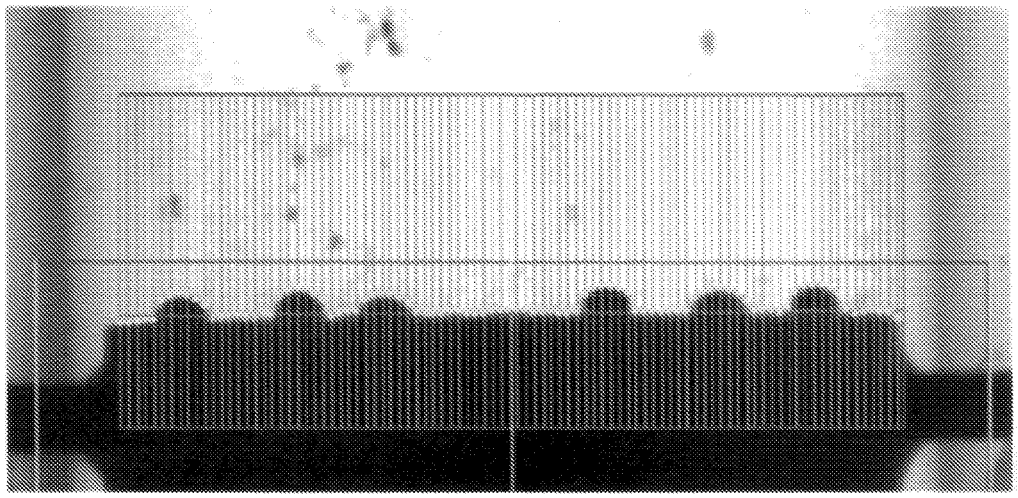

*The image above is equivalent to the black and white line drawing of an example image of a refined plunger ROI that is aligned with the top of the plunger to facilitate one-dimensional (1D) edge detection, as shown in FIG. 9A.*

*The image above is equivalent to the black and white line drawing of an example image of a refined plunger ROI that is aligned with the top of the plunger to facilitate one-dimensional (1D) edge detection, as shown in FIG. 9B.*

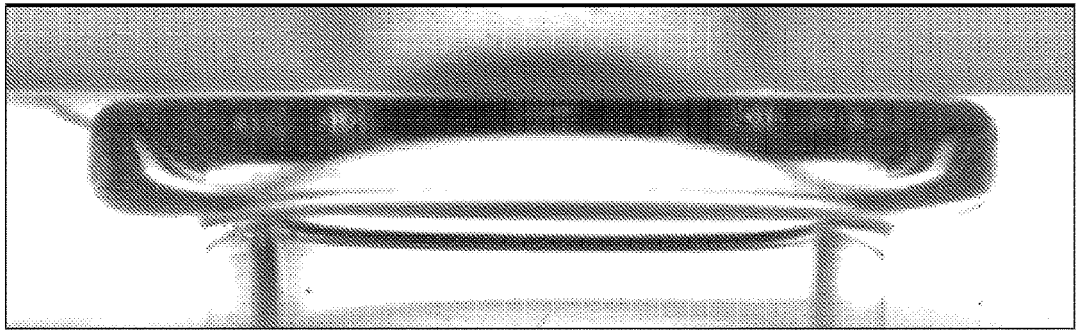
*The image above is an example of an unprocessed ROI image of a 2.25mL flange. Note that the top of the flange is "touching" the darker areas in the tray in the image background.*

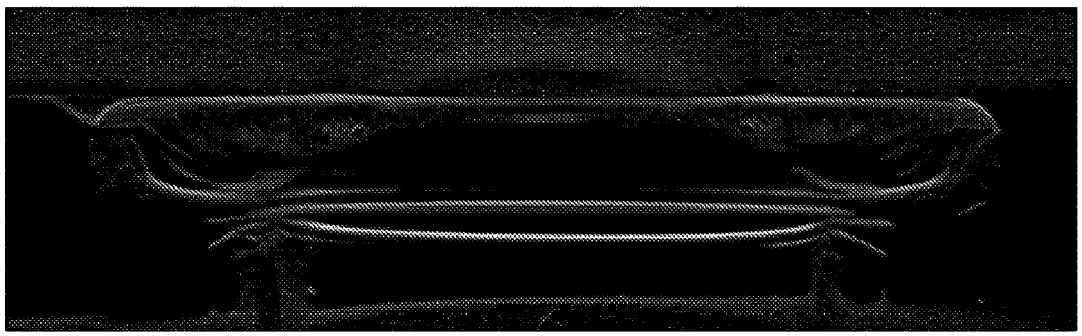
*The image above is an example of the top image after being convoluted with a 3x3 kernel.*

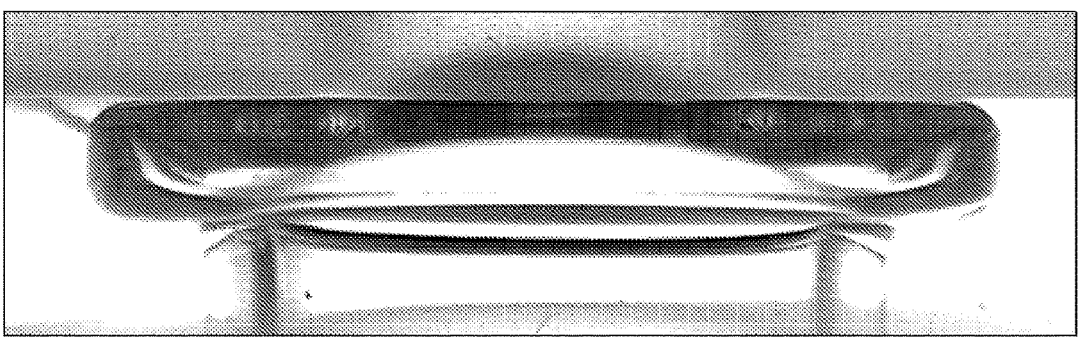
*The image above is an example of subtracting the convolution image (center) from the original image (top). Note that the top edge of the flange has been darkened and the contrast sharpened.*

What is claimed is:

1. A method for performing plunger depth inspection for a vessel having a plunger, comprising:
    acquiring, via an imager, an image of the vessel including a reference point region of interest (ROI) that encompasses an image of a reference point from which to measure plunger depth, and an initial plunger ROI that encompasses an image of the plunger;
    generating, via a controller, a binarized reference point image based upon a blob analysis of the reference point ROI;
    calculating, via the controller, a vessel edge within the binarized reference point image;
    aligning, via the controller, a refined plunger ROI with the top of the plunger within the initial plunger ROI using a matching plunger image template from among a plurality of plunger image templates;
    calculating, via the controller, a plunger edge within the refined plunger ROI; and
    calculating, via the controller, a depth of the plunger within the vessel based upon the vessel edge and the plunger edge.

2. The method of claim 1, wherein the act of generating the binarized reference point image comprises:
    applying intensity thresholding and a closing algorithm to the reference point ROI to generate the binarized reference point image.

3. The method of claim 1, wherein the act of generating the binarized reference point image comprises:
    scanning horizontal rows within the binarized reference point image to identify falling-edge pixel transitions and rising-edge pixel transitions, the falling-edge pixel transitions representing a transition from a binary value of 1 to a binary value of 0, and the rising-edge pixel transitions representing a transition from a binary value of 0 to a binary value of 1;
    identifying, from within each scanned horizontal row, pairs of falling-edge pixel transitions and rising-edge pixel transitions; and
    adjusting, within each scanned horizontal row, values of pixels between the pairs of falling-edge pixel transitions and rising-edge pixel transitions from a binary value of 0 to a binary value of 1.

4. The method of claim 1, further comprising:
    identifying, via the controller, the matching plunger image template using a greyscale value pyramid template matching algorithm.

5. The method of claim 1, wherein the act of calculating the plunger edge within the refined plunger ROI comprises:
    dividing the top of the refined plunger ROI into a plurality of columns;
    performing one-dimensional (1D) edge-detection on each of the plurality of columns to determine, for each column, a y-coordinate value associated with an upper edge of the plunger; and
    calculating the uppermost plunger edge within the refined plunger ROI based upon the y-coordinate value associated with the upper edge of the plunger in each of the plurality of columns.

6. The method of claim 5, wherein the act of calculating the plunger edge within the refined plunger ROI further comprises:
    binning the y-coordinate value in each of the plurality of columns in accordance with a histogram according to y-coordinate values;
    removing bins having less than a threshold number of elements to generate a constrained set of y-coordinate values; and
    calculating the uppermost plunger edge within the refined plunger ROI based upon the constrained set of y-coordinate values.

7. The method of claim 6, wherein the act of calculating the plunger edge within the refined plunger ROI further comprises:
    applying a best-fit-line algorithm to the constrained set of y-coordinate values.

8. An automated visual inspection (AVI) system, comprising:
    an imager configured to acquire an image of each of a plurality of syringes in a sequential manner to generate a plurality of syringe images, each of the plurality of syringes having a respective flange and plunger;
    a stage configured to receive a tray containing the plurality of syringes and to incrementally move the tray to facilitate sequential imaging of the plurality of syringes by the imager; and
    a controller configured to, for each sequentially acquired syringe image from among the plurality of syringe images:
        perform an image analysis of a flange region of interest (ROI) that encompasses the flange within the syringe image to generate a binarized flange image;
        identify a plunger ROI that is aligned with a top of the plunger within the syringe image using a matching plunger image template from among a plurality of plunger image templates;
        calculate an uppermost flange edge within the binarized flange image;
        calculate an uppermost plunger edge within the plunger ROI; and
        calculate a depth of the plunger within the syringe based upon the uppermost flange edge and the uppermost plunger edge.

9. The AVI system of claim 8, wherein the image analysis of the flange ROI is a blob analysis.

10. The AVI system of claim 8, wherein the image analysis of the flange ROI to generate the binarized flange image includes a closing algorithm to remove artifacts and fill voids within the binarized flange image.

11. The AVI system of claim 8, wherein the image analysis of the flange ROI to generate the binarized flange image includes:
    scanning horizontal rows within the binarized flange image to identify falling-edge pixel transitions and rising-edge pixel transitions, the falling-edge pixel transitions representing a transition from a binary value of 1 to a binary value of 0, and the rising-edge pixel transitions representing a transition from a binary value of 0 to a binary value of 1;
    identifying, from within each scanned horizontal row, pairs of falling-edge pixel transitions and rising-edge pixel transitions; and
    adjusting, within each scanned horizontal row, values of pixels between the pairs of falling-edge pixel transitions and rising-edge pixel transitions from a binary value of 0 to a binary value of 1.

12. The AVI system of claim 8, wherein the controller is further configured to identify the matching plunger image template using a greyscale value pyramid template matching algorithm.

13. The AVI system of any one of claim 8, wherein the act of calculating the uppermost plunger edge within the plunger ROI comprises:
    dividing the top of the plunger ROI into a plurality of columns;

performing one-dimensional (1D) edge-detection on each of the plurality of columns to determine, for each column, a y-coordinate value associated with an upper edge of the plunger; and calculating the uppermost plunger edge within the plunger ROI based upon the y-coordinate value associated with the upper edge of the plunger in each of the plurality of columns.

14. A tangible, non-transitory, computer-readable medium storing instructions on a computing device that, when executed by one or more processors associated with the computing device, cause the computing device to:

acquire an image of a syringe having a flange and a plunger;

calculate an uppermost flange edge within the image of the syringe;

match an image of the plunger within the image of the syringe to a matching plunger image template from among a plurality of plunger image templates;

align a plunger ROI with the top of the plunger within the image of the syringe using the matching plunger image template;

calculate an uppermost plunger edge associated with the image of the plunger within the plunger ROI; and calculate a depth of the plunger within the syringe based upon the uppermost flange edge and the uppermost plunger edge.

15. The tangible, non-transitory, computer-readable medium of claim 14, wherein the image of the syringe includes a flange region of interest (ROI) that encompasses an image of the flange, and wherein the instructions to calculate the uppermost flange edge within the image of the syringe include instructions that, when executed by the one or more processors associated with the computing device, cause the computing device to:

generate a binarized flange image based upon a blob analysis of the flange ROI, and calculate the uppermost flange edge within the image as the uppermost flange edge within the binarized flange image.

16. The tangible, non-transitory, computer-readable medium of claim 15, wherein the instructions to calculate the uppermost flange edge within the image of the syringe further include instructions that, when executed by the one or more processors associated with the computing device, cause the computing device to execute a closing algorithm to remove artifacts and to fill voids within the binarized flange image.

17. The tangible, non-transitory, computer-readable medium of claim 14, wherein the instructions to match the image of the plunger to the matching plunger image template further include instructions that, when executed by the one or more processors associated with the computing device, cause the computing device to execute a greyscale value pyramid template matching algorithm.

18. The tangible, non-transitory, computer-readable medium of claim 14, wherein the instructions to calculate the uppermost plunger edge further include instructions that, when executed by the one or more processors associated with the computing device, cause the computing device to perform one-dimensional (1D) edge-detection on each of a plurality of evenly-divided columns within the plunger ROI to determine, for each column, a y-coordinate value associated with an upper edge of the plunger, and to calculate the uppermost plunger edge within the refined plunger ROI based upon the y-coordinate value associated with the upper edge of the plunger in each of the plurality of evenly-divided columns.

19. The tangible, non-transitory, computer-readable medium of claim 18, wherein the instructions to calculate the uppermost plunger edge further include instructions that, when executed by the one or more processors associated with the computing device, cause the computing device to calculate the uppermost plunger edge based upon a constrained set of y-coordinate values that are selected in accordance with a histogram grouping of the y-coordinate values from each of the plurality of evenly-divided columns.

20. The tangible, non-transitory, computer-readable medium of claim 19, wherein the instructions to calculate the uppermost plunger edge further include instructions that, when executed by the one or more processors associated with the computing device, cause the computing device to apply a best-fit-line algorithm to the constrained set of y-coordinate values.

* * * * *